(12) United States Patent
Mitragotri et al.

(10) Patent No.: US 8,287,483 B2
(45) Date of Patent: Oct. 16, 2012

(54) METHOD AND APPARATUS FOR ENHANCEMENT OF TRANSDERMAL TRANSPORT

(75) Inventors: Samir S. Mitragotri, Goleta, CA (US); Joseph Kost, Cambridge, MA (US); Scott C. Kellogg, Boston, MA (US); Nicholas F. Warner, Belmont, MA (US); Tuan A. Elstrom, Lake Bluff, IL (US)

(73) Assignee: Echo Therapeutics, Inc., Philadelphia, PA (US)

( * ) Notice: Subject to any disclaimer, the term of this patent is extended or adjusted under 35 U.S.C. 154(b) by 1948 days.

(21) Appl. No.: 10/792,862

(22) Filed: Mar. 5, 2004

(65) Prior Publication Data

US 2004/0236268 A1 Nov. 25, 2004

Related U.S. Application Data

(62) Division of application No. 09/868,442, filed as application No. PCT/US99/30065 on Dec. 17, 1999, now abandoned.

(60) Provisional application No. 60/142,975, filed on Jul. 12, 1999, provisional application No. 60/142,951, filed on Jul. 12, 1999, provisional application No. 60/142,950, filed on Jul. 12, 1999, provisional application No. 60/142,941, filed on Jul. 12, 1999, provisional application No. 60/112,953, filed on Dec. 18, 1998.

(51) Int. Cl.
*A61B 17/20* (2006.01)
*A61M 31/00* (2006.01)

(52) U.S. Cl. .......................................... 604/22; 604/503

(58) Field of Classification Search .................. 604/20, 604/501, 890.1, 892.1, 46, 47, 22, 503; 600/306, 600/358
See application file for complete search history.

(56) References Cited

U.S. PATENT DOCUMENTS

| | | | |
|---|---|---|---|
| 3,508,540 A * | 4/1970 | Cavallari, Jr. et al. | ........ 600/547 |
| 3,551,554 A | 12/1970 | Herschler | |
| 3,711,602 A | 1/1973 | Herschler | |
| 3,711,606 A | 1/1973 | Herschler | |
| 3,828,769 A | 8/1974 | Mettler | |
| 4,002,221 A | 1/1977 | Buchalter | |
| 4,020,830 A | 5/1977 | Johnson et al. | |
| 4,127,125 A | 11/1978 | Takemoto et al. | |

(Continued)

FOREIGN PATENT DOCUMENTS

CA 2196746 8/1991

(Continued)

OTHER PUBLICATIONS

Notification of Transmittal of the International Search Report and the Written Opinion of the International Searching Authority, or the Declaration, dated Jun. 23, 2008.

(Continued)

*Primary Examiner* — Nicholas Lucchesi
*Assistant Examiner* — Nathan R Price
(74) *Attorney, Agent, or Firm* — Pabst Patent Group LLP

(57) ABSTRACT

According to the present invention, a method for enhancing transdermal transport is disclosed. The method includes the steps of increasing a permeability of an area of a membrane with a permeabilizing device. The membrane may be, inter alia, biologic skin or synthetic skin. The permeabilizing device may be an ultrasound-producing device. A substance is transported into and through the area of the membrane. The substance may be a drug, a vaccine, or a component of interstitial fluid.

22 Claims, 19 Drawing Sheets

U.S. PATENT DOCUMENTS

| | | | |
|---|---|---|---|
| 4,144,317 A | 3/1979 | Higuchi et al. | |
| 4,144,646 A | 3/1979 | Takemoto et al. | |
| 4,176,664 A | 12/1979 | Kalish | |
| 4,249,531 A | 2/1981 | Heller et al. | |
| 4,280,494 A | 7/1981 | Cosgrove, Jr. | |
| 4,309,989 A | 1/1982 | Fahim | |
| 4,372,296 A | 2/1983 | Fahim | |
| 4,457,748 A | 7/1984 | Lattin | |
| 4,537,776 A | 8/1985 | Cooper | |
| 4,557,943 A | 12/1985 | Rosler et al. | |
| 4,563,184 A | 1/1986 | Korol | |
| 4,595,011 A | 6/1986 | Phillips | |
| 4,646,725 A | 3/1987 | Moasser | |
| 4,657,543 A | 4/1987 | Langer et al. | |
| 4,683,242 A | 7/1987 | Poser | |
| 4,698,058 A | 10/1987 | Greenfeld et al. | |
| 4,702,732 A | 10/1987 | Powers et al. | |
| 4,732,153 A | 3/1988 | Phillips | |
| 4,767,402 A | 8/1988 | Kost et al. | |
| 4,779,806 A | 10/1988 | Langer et al. | |
| 4,780,212 A | 10/1988 | Kost et al. | |
| 4,786,277 A | 11/1988 | Powers | |
| 4,787,070 A | 11/1988 | Suzuki et al. | |
| 4,787,888 A | 11/1988 | Fox | |
| 4,820,720 A | 4/1989 | Sanders et al. | |
| 4,821,733 A | 4/1989 | Peck | |
| 4,821,740 A | 4/1989 | Tachibana et al. | |
| 4,834,978 A | 5/1989 | Nuwayser | |
| 4,855,298 A | 8/1989 | Yamada et al. | |
| 4,860,058 A | 8/1989 | Kobayashi et al. | |
| 4,863,970 A | 9/1989 | Patel et al. | |
| 4,866,050 A | 9/1989 | Ben-Amoz | |
| 4,933,062 A | 6/1990 | Shaw et al. | |
| 4,948,587 A | 8/1990 | Kost et al. | |
| 4,953,552 A | 9/1990 | DeMarzo | |
| 4,953,565 A | 9/1990 | Tachibana et al. | |
| 4,970,145 A | 11/1990 | Bennetto et al. | |
| 4,981,779 A | 1/1991 | Wagner | |
| 4,986,271 A | 1/1991 | Wilkins | |
| 5,001,051 A | 3/1991 | Miller et al. | |
| 5,006,342 A | 4/1991 | Cleary et al. | |
| 5,007,438 A | 4/1991 | Tachibana et al. | |
| 5,016,615 A | 5/1991 | Driller et al. | |
| 5,019,034 A | 5/1991 | Weaver et al. | |
| 5,036,861 A | 8/1991 | Sembrowich et al. | |
| 5,050,604 A | 9/1991 | Reshef et al. | |
| 5,069,908 A | 12/1991 | Henley | |
| 5,076,273 A | 12/1991 | Schoendorfer et al. | |
| 5,078,144 A | 1/1992 | Sekino et al. | |
| 5,082,786 A | 1/1992 | Nakamoto | |
| 5,086,229 A | 2/1992 | Rosenthal et al. | |
| 5,115,805 A | 5/1992 | Bommannan et al. | |
| 5,118,404 A | 6/1992 | Saito | |
| 5,119,819 A | 6/1992 | Thomas et al. | |
| 5,120,544 A | 6/1992 | Henley | |
| 5,134,057 A | 7/1992 | Kuypers et al. | |
| 5,135,753 A | 8/1992 | Baker et al. | |
| 5,139,023 A | 8/1992 | Stanley et al. | |
| 5,140,985 A | 8/1992 | Schroeder et al. | |
| 5,161,532 A | 11/1992 | Joseph | |
| 5,165,407 A | 11/1992 | Wilson et al. | |
| 5,165,418 A | 11/1992 | Tankovich | |
| 5,171,215 A | 12/1992 | Flanagan | |
| 5,197,946 A | 3/1993 | Tachibana | |
| 5,215,520 A | 6/1993 | Shroot et al. | |
| 5,215,887 A | 6/1993 | Saito | |
| 5,230,334 A | 7/1993 | Klopotek | |
| 5,231,975 A | 8/1993 | Bommannan et al. | |
| 5,236,410 A | 8/1993 | Granov et al. | |
| 5,250,419 A | 10/1993 | Bernard et al. | |
| 5,267,985 A | 12/1993 | Shimada et al. | |
| 5,279,543 A | 1/1994 | Glikfeld et al. | |
| 5,282,785 A | 2/1994 | Shapland et al. | |
| 5,286,254 A | 2/1994 | Shapland et al. | |
| 5,315,998 A | 5/1994 | Tachibana et al. | |
| 5,323,769 A | 6/1994 | Bommannan et al. | |
| 5,330,756 A | 7/1994 | Steuart et al. | |
| 5,346,814 A * | 9/1994 | Hahn et al. ..................... 435/35 |
| 5,362,307 A | 11/1994 | Guy et al. | |
| 5,364,838 A | 11/1994 | Rubsamen | |
| 5,386,837 A | 2/1995 | Sterzer | |
| 5,401,237 A | 3/1995 | Tachibana et al. | |
| 5,405,366 A | 4/1995 | Fox et al. | |
| 5,405,614 A | 4/1995 | DAngelo et al. | |
| 5,413,550 A | 5/1995 | Castel | |
| 5,415,629 A | 5/1995 | Henley | |
| 5,421,816 A | 6/1995 | Lipkovker | |
| 5,429,735 A | 7/1995 | Johnson et al. | |
| 5,443,080 A | 8/1995 | DAngelo et al. | |
| 5,445,611 A | 8/1995 | Eppstein et al. | |
| 5,458,140 A | 10/1995 | Eppstein et al. | |
| 5,470,582 A | 11/1995 | Supersaxo et al. | |
| 5,534,496 A | 7/1996 | Lee et al. | |
| 5,538,503 A | 7/1996 | Henley | |
| 5,569,198 A | 10/1996 | Racchini | |
| 5,573,778 A | 11/1996 | Therriault et al. | |
| 5,582,184 A | 12/1996 | Erickson et al. | |
| 5,582,586 A | 12/1996 | Tachibana et al. | |
| 5,617,851 A | 4/1997 | Lipkovker | |
| 5,618,275 A | 4/1997 | Bock | |
| 5,626,554 A | 5/1997 | Ryaby et al. | |
| 5,636,632 A | 6/1997 | Bommannan et al. | |
| 5,646,221 A | 7/1997 | Inagi et al. | |
| 5,655,539 A | 8/1997 | Wang et al. | |
| 5,656,016 A | 8/1997 | Ogden | |
| 5,658,247 A * | 8/1997 | Henley ........................... 604/20 |
| 5,667,487 A | 9/1997 | Henley | |
| 5,722,397 A | 3/1998 | Eppstein | |
| 5,730,714 A | 3/1998 | Guy et al. | |
| 5,735,273 A | 4/1998 | Kurnik et al. | |
| 5,746,217 A | 5/1998 | Erickson et al. | |
| 5,771,890 A | 6/1998 | Tamada | |
| 5,814,599 A | 9/1998 | Mitragotri et al. | |
| 5,820,570 A | 10/1998 | Erickson et al. | |
| 5,827,183 A | 10/1998 | Kurnik et al. | |
| 5,833,647 A | 11/1998 | Edwards | |
| 5,851,438 A | 12/1998 | Chan | |
| 5,885,211 A | 3/1999 | Eppstein et al. | |
| 5,902,603 A | 5/1999 | Chen et al. | |
| 5,906,830 A | 5/1999 | Farinas et al. | |
| 5,947,921 A | 9/1999 | Johnson et al. | |
| 5,961,451 A | 10/1999 | Reber et al. | |
| 5,989,409 A | 11/1999 | Kurnik et al. | |
| 6,002,961 A | 12/1999 | Mitragotri et al. | |
| 6,009,343 A | 12/1999 | Shain et al. | |
| 6,018,678 A | 1/2000 | Mitragotri et al. | |
| 6,032,060 A * | 2/2000 | Carim et al. .................. 600/372 |
| 6,041,252 A * | 3/2000 | Walker et al. ................... 604/20 |
| 6,041,253 A | 3/2000 | Kost et al. | |
| 6,148,232 A * | 11/2000 | Avrahami ........................ 604/20 |
| 6,190,315 B1 | 2/2001 | Kost et al. | |
| 6,234,990 B1 | 5/2001 | Rowe et al. | |
| 6,251,083 B1 | 6/2001 | Yum et al. | |
| 6,283,926 B1 | 9/2001 | Cunningham et al. | |
| 6,299,578 B1 | 10/2001 | Kurnik et al. | |
| 6,309,351 B1 | 10/2001 | Kurnik et al. | |
| 6,398,753 B2 | 6/2002 | McDaniel | |
| 6,468,229 B1 | 10/2002 | Grace et al. | |
| 6,482,604 B2 | 11/2002 | Kwon | |
| 6,487,447 B1 | 11/2002 | Weimann et al. | |
| 6,491,657 B2 | 12/2002 | Rowe et al. | |
| 6,503,198 B1 | 1/2003 | Aronowtiz et al. | |
| 6,535,753 B1 | 3/2003 | Raskas | |
| 6,540,675 B2 | 4/2003 | Aceti et al. | |
| 6,546,378 B1 * | 4/2003 | Cook ............................... 706/12 |
| 2003/0100846 A1 | 5/2003 | Custer et al. | |
| 2004/0039418 A1 | 2/2004 | Elstrom et al. | |
| 2004/0171980 A1 | 9/2004 | Mitragotri et al. | |

FOREIGN PATENT DOCUMENTS

| | | |
|---|---|---|
| CA | 1324051 | 11/1993 |
| CA | 2167393 | 1/1995 |
| CA | 2226176 | 1/1997 |
| CA | 2229480 | 3/1997 |
| CA | 2212826 | 7/1997 |
| CA | 2075624 | 11/1997 |
| DE | 2756460 | 6/1979 |

| | | |
|---|---|---|
| EP | 0 043 738 | 1/1982 |
| EP | 0 245 535 | 11/1987 |
| EP | 0 246 341 | 11/1987 |
| EP | 0 247 850 | 12/1987 |
| EP | 0 278 074 | 8/1988 |
| EP | 0 304 304 | 2/1989 |
| EP | 0 368 408 | 5/1990 |
| EP | 0 453 283 | 10/1991 |
| EP | 0 495 531 | 7/1992 |
| EP | 0 513 789 | 11/1992 |
| EP | 0 612 525 | 8/1994 |
| EP | 0 625 360 | 11/1994 |
| EP | 0 649 628 | 4/1995 |
| EP | 0 736 305 | 10/1996 |
| EP | 0 847 775 | 6/1998 |
| GB | 1577551 | 2/1977 |
| GB | 1 577 551 | 10/1980 |
| GB | 2153223 | 12/1984 |
| JP | 59-95060 | 5/1984 |
| JP | 62133937 | 6/1987 |
| JP | 3170172 | 7/1991 |
| SU | 445433 | 11/1974 |
| SU | 556805 | 6/1977 |
| SU | 591186 | 1/1978 |
| SU | 506421 | 2/1978 |
| SU | 910157 | 3/1982 |
| WO | WO 87/07295 | 12/1987 |
| WO | WO 88/00001 | 1/1988 |
| WO | WO 90/01971 | 3/1990 |
| WO | WO 90/15568 | 12/1990 |
| WO | WO 91/12772 | 9/1991 |
| WO | WO 92/13567 | 8/1992 |
| WO | WO 94/05368 | 8/1992 |
| WO | WO 92/14449 | 9/1992 |
| WO | WO 93/05096 | 3/1993 |
| WO | WO 93/20745 | 10/1993 |
| WO | WO 94/08655 | 4/1994 |
| WO | WO 95/02357 | 1/1995 |
| WO | WO 96/00110 | 1/1996 |
| WO | WO 97/02811 | 1/1997 |
| WO | WO 97/04832 | 2/1997 |
| WO | WO 97/10499 | 3/1997 |
| WO | WO 97/13548 | 4/1997 |
| WO | WO 97/18851 | 5/1997 |
| WO | WO 97/24059 | 7/1997 |
| WO | WO 97/30628 | 8/1997 |
| WO | WO 97/30749 | 8/1997 |
| WO | WO 98/00194 | 1/1998 |
| WO | WO 98/17184 | 4/1998 |
| WO | WO 98/20331 | 5/1998 |
| WO | WO 98/28037 | 7/1998 |
| WO | WO 98/34541 | 8/1998 |
| WO | WO 98/42252 | 10/1998 |
| WO | WO 99/34857 | 7/1999 |
| WO | WO 99/34858 | 7/1999 |
| WO | WO 99/39763 | 8/1999 |
| WO | WO 00/04821 | 2/2000 |
| WO | WO 00/35351 | 6/2000 |
| WO | WO 00/35357 | 6/2000 |
| WO | WO 01/70330 | 9/2001 |

OTHER PUBLICATIONS

U.S. Appl. No. 10/411,156.
U.S. Appl. No. 10/792,886.
U.S. Appl. No. 09/868,442.
Agrawl, C.M. et al., "The effects of ultrasound irradiation on a biodegradable 50-50% copolymer of polylactic and polyglycolic acids," 28 Journal of Biomedical Materials Research 851-859 (1994).
Albin et al., "Theoretical and Experimental Studies of Glucose Sensitive Membranes," 6 Journal of Controlled Release 267-291 (1987).
Allcock, H., et al., "Activity of Urea Amidohydrolase Immobilized within Poly[di(methoxy-ethoxyethoxy)phosphazene Hydrogels," Biomaterials, vol. 15, No. 7, pp. 502-506 (Jun. 1994).
Apfel, R. F., "Possibility of Microcavitation from Diagnostic Ultrasound," IEEE Trans. Ultrason Ferroelectrics Freq. Control UFFC 33:139-142 (1986).
Asakura et al. "Immobilization of Glucose Oxidase on Nonwoven Fabrics with Bombyx mori Silk Fibroin Gel," Journal of Applied Polymer Science, vol. 46, No. 1, pp. 49-53 (Sep. 5, 1992).
Aungst et al., "Contributions of Drug Solubilization, Partitioning, Barrier Disruption, and Solvent Permeation to the Enhancement of Skin Permeation of Various Compounds with Fatty Acids and Amines," Pharm. Res. 7:712-718 (1990).
Barry, "Mode of Action of Penetration Enhancers in Human Skin," J. Controlled Rel. 6:85-97 (1987).
Bhat, et al., "Optimization of delivery of betamethasone-dipropionate from skin preparation," Indian Drugs 32:211-14 (1995).
Blackshear, "Implantable Drug-Delivery Systems," Scientific America, p. 66-73 (604193) (Dec. 1979).
Bommer, et al., "Subcutaneous Erythropoietin" The Lancet 406 (1988).
Alain Boucaud et al., "Clinical, histologic, and electron microscopy study of skin exposed to low frequency ultrasound," The Anatomical Record, vol. 264, No. 1, pp. 114-119 (Sep. 2001).
A. Boucaud et al., "In vitro study of low-frequency ultrasound-enhanced transdermal transport of fentanyl and caffeine across human and hairless rat skin," International J. Pharmaceuticals, vol. 228, Nos. 1-2, pp. 69-77 (Oct. 2001).
Burnette, R.R., "Iontophoresis," Transdermal Drug Delivery Development Issues and Research Initiatives 247-291 (Hadgraft and Guv. Editors, Marcel Dekker, 1989).
Philip S. Burton et al., "Metabolism and Transport of Peptide Across Intestinal Mucosa," 14 Proceed. Intern. Symp. Control. Rel. Bioact. Mater 6 (Controlled Release Society, Inc. 1987).
Etienne Camel, "Ultrasound," Percutaneous Penetration Enhancers 369-382 (Eric W. Smith et al. eds. 1995).
Gary W. Cleary, "Transdermal Controlled Release Systems," Medical Applications of Controlled Release 203-251 (Langer and Wise, Editors, CRCPress 1984).
Clegg and Vaz, "Translational diffusion of proteins and lipids in artificial lipid bilayer membranes, A comparison of experiment with theory," Progress in Protein-Lipid Interactions Watts, ed. Chapter 5:173-229 (Elsvier, NY 1985).
D'Emanuele, et al., "An Investigation of the Effects of Ultrasound on Degradable Polyanhydride Matrices," 25 Macromolecules 511-515 (1992).
J. Davis et al., "Characterization of Recombinant Human Erythropoietin Produced in Chinese Hamster Ovary Cells," Biochemistry 26:2633-2638 (1987).
Domb, et al., "Polyanhydrides-Sysnthesis and Characterization," 107 Advances in Polymer Science: 93-141 (1993).
Ebert et al., "Transbuccal Absorption of Diclofenac Sodium in a Dog Model," Controlled Release Technology Pharmaceutical Application 310-321 (Lee, et al. Editors, American Chemical Society, 1987).
R.M. Eggerth et al., "Evaluation of Hamster Cheek Pouch as a Model for Buccal Absorption," 14 Proceed. Intern. Symp. Rel. Bioact. Mater. 180-181 (Controlled Release Society, Inc. 1987).
Egorov, E.A. et al., "Use of the Variants of the Pharmacophysical Influence in Ophthalmology," 102 Ophthalmology Journal #2 (1992).
J.J. Elias, "The Microscopic Structure of the Epidermis and Its Derivatives," Percutaneous Absorption: Mechanisms—Methodology—Drug Delivery 1-12 (1989).
Eppstein, D.A. et al., "Alternative Delivery Systems for Peptides and Proteins as Drugs," 5 CRC Reviews in Therapeutic Drug Carrier Systems 99-139 (1988).
Eppstein, D.A. et al., "Applications of Liposome Formulations for Antimicrobial/Antiviral Therapy," Liposomes as Drug Carriers 311-323 (John Wiley & Sons 1988).
Eppstein, D.A. et al., "Medical Utility of Inteferons: Approaches to Increasing Therapeutic Efficacy" 7 Pharmacy International 195-199 (1986).
G.L. Flynn, "Mechanism of Percutaneous Absorpotion from Physicochemical Evidence," Percutaneous Absorption: Mechanisms—Methodology—Drug Delivery, pp. 27-51 (1989).
R.M. Friedman, "Interferons: A Primer," ISBN 0-12-268280-7 (Academic Press, NY 1981).
Gaertner, W., "Frequency Dependence of Ultrasonic Cavitation," J. Acoust. Soc. Am. 26:977-980 (1954).

Ghanem et al., "The effects of ethanol on the transport of lipophilic and polar permeants across hairless mouse skin: Methods/validation of a novel approach," Int. J. Pharm. 78:137-156 (1992).

Grups and Frohmuller, "Cyclic Interferon Gamma Treatment of Patients with Metastatic Renal Carcinoma," J. Med. 64(3):218-220 (1989).

Hansch and Leo, "Substitutent Constants for Correlation Analysis in Chemistry and Biology" (1979).

Heller, J., et al. "Controlled Drug Release by Polymer Dissolution II Enzyme-Mediated Delivery Device," Journal of Pharmaceutical Sciences, vol. 68, No. 7, pp. 919-921 (Jul. 1979).

Mark E. Johnson et al., "Synergistic Effects of Chemical Enhancers and Therapeutic Ultrasound on Transdermal Drug Delivery," 85 J. Pharmaceutical Sciences 670-679 (Jul. 1996).

H.E. Junginger et al., "Visualization of Drug Transport Across Human Skin and the Influence of Penetration Enhancers," Drug Permeation Enhancement 59-89 (1994).

Kamath, et al., "Biodegradable hydrogels in Drug Delivery," 11 Advanced Drug Delivery Reviews 59-84 (1993).

G.B. Kasting et al., "Prodrugs for Dermal Delivery: Solubility, Molecular Size, and Functional Group Effects," Prodrugs: Topical and Ocular Delivery 117-161 (1992).

A.D. Keith and W. Snipes, "Polymeric Carriers for Active Agents," Transdermal and Related Drug Delivery Systems pp. 223-279 (D.A. Jones ed. 1984).

Kost and Langer, "Ultrasound-Mediated Transdermal Drug Delivery," Topical Drug Bioavailability Bioequivalence and Penetration 91-104 (1993).

J. Kost et al., "Ultrasound Effect on Transdermal Drug Delivery," Ben Gurion University, Dept. of Chem. Engineering, Beer Sheva Israel MIT, Dept. of Applied Biological Sciences, Cambridge, MA.

Kost, J., et al., "Glucose-Sensitive Membranes Containing Glucose Oxidase: Activity, Swelling, and Permeability Studies," Journal of Biomedical Materials Research, vol. 19, pp. 1117-1133 (1985).

Joseph Kost et al., "Synergistic Effect of Electric Field and Ultrasound on Transdermal Transport," Pharmaceutical Research, vol. 13, No. 4, pp. 633-638 (1996).

L.P. Krall, "World Book of Diabetes in Practice," vol. 3, pp. 2-7 (Elsvier, 1988).

Langer et al., "Chemical and Physical Structure of Polymers as Carriers for Controlled Release of Bioactive Agents: A Review," Journal of Macromolecular Science, Reviews on Macromolecular Chemistry and Physics, C23(1), 61-126 (1983).

Lee & Rashi, "Nasal Peptide and Protein Absorption Promotors: Aminopeptidase Inhibition as a Predictor of Absorption Enhancement Potency of Bile Salts," Proceed. Intern. Symp. Control. Rel. Bioact. Mater. 14, 53-54 (1987).

Lee et al., "Protease Inhibition as an Additional Mechanism for the Nasal Absorpotion Enhancement Effect of Sodium Taurodihydrofusidate," Proceed. Intern. Symp. Control. Rel. Bioact. Mater. 14, 55-56 (1987).

Lesho et al., "A Photopatterned Glucose Responsive Hydrogel for Use in a Conductimetric Sensor," Biomaterials for Drug and Cell Delivery, Materials Research Society Symposium Proceedings, vol. 331, pp. 193-198 (1994).

Levy et al., "Effect of Ultrasound on Transdermal Drug Delivery to Rats and Guinea Pigs," J. Clin. Invest. 83:2074-2078 (1989).

Liu et al., "Experimental Approach to Elucidate the Mechanism of Ultrasound-Enhanced Polymer Erosion and Release of Incorporated Substances," 25 Macromolecules 123-128 (1992).

Liu, et al., "Cotransport of Estradiol and Ethanol Through Human Skin in Vitro: Understanding the Permeant/Enhancer Flux Relationship," Pharmaceutical Research 8:938-944 (1991).

Machluf and Kost, "Ultrasonically enhanced transdermal drug delivery, Experimental approaches to elucidate the mechanism," J. Biomater. Sci. Polymer Edn. 5:147-156 (1993).

Mak et al., "Oleic Acid Concentration and Effect in Human Stratum Corneum: Non-Invasive Determination by Attenuated Total Reflectance Infrared Spectroscopy in Vivo,": J. Controlled Rel. 12:67-75 (1990).

Mezei, Michael, "Liposomes as a Skin Drug Delivery System," Topics in Pharmaceutical Sciences pp. 345-357 (1985).

Mitragotri et al., "A Mechanistic Study of Ultrasonically-Enhanced Transdermal Drug Delivery," J. Pharm. Sci. vol. 84, No. 6, pp. 697-706 (1995).

Mitragotri et al., "Ultrasound-Mediated Transdermal Protein Delivery," Science 269:850-853 (Aug. 11, 1995).

Samir Mitragotri et al., "Sonophoresis: Enhanced Transdermal Drug Delivery by Application of Ultrasound," 14 Encyclopedia of Pharmaceutical Technology 103-122 (1996).

Mitragotri, S. et al., "Synergistic Effect of Low-frequency Ultrasound and Sodium Lauryl Sulfate on Transdermal Transport," J. Pharm. Sci. vol. 89, No. 7, pp. 892-900 (2000).

S. Mitragotri, "Synergistic Effect of Enhancers for Transdermal Drug Delivery," Pharm Res. vol. 17, No. 11, pp. 1354-1359 (2000).

S. Mitragotri and Joseph Kost, "Transdermal Delivery of Heparin and Low-Molecular Weight Heparin Using Low-Frequency Ultrasound," Pharmaceutical Research, vol. 18, No. 8, pp. 1151-1156 (Aug. 2001).

Miyazaki, et al., "Controlled Drug Release by Ultrasound Irradiation," Chemical & Pharmaceutical Bulletin, 33(1), pp. 428-431 (1985).

D. Monti et al., "Comparison of the effect of ultrasound of chemical enhancers on transdermal permeation of caffeine and morphine through hairless mouse skin in vitro," International J. Pharmaceuticals, vol. 229, Nos. 1-2, pp. 131-137 (Oct. 2001).

Y. Morimoto et al., "Prediction of Skin Permeability of Drugs: Comparison of Human and Hairless Rat Skin," J. Pharm. Pharmacol. 44:634-639 (1991).

I.A. Murav'ev et al., "Mechanism of the Release of Pharmaceutical Substances from Ointment Bases by Ultrasound", Chemical Abstracts, vol. 84, No. 4, Jan. 26, 1976, p. 333, Abstract No. 22054g (Jan. 26, 1996).

T. Nagai et al., "Buccaal/Gingival Drug Delivery Systems," Journal of Controlled Release 6:353-360 (1987).

J. Newman et al., "Hydrocortisone Phonophoresis," J. Am. Pod. Med. Assoc. 82:432-435 (1992).

Olanoff and Gibson, "Method to Enhance Intranasal Peptide Delivery," Controlled Release Technology Pharmaceutical Application 301-309 (1987).

Ongpipattanankul et al., "Evidence that Oleic Acid Exists in a Separate Phase Within Stratum Corneum Lipids," Pharm. Res. 8:350-354 (1991).

Otsuka, et al., "Use of Ultrasonic Waves in Pharmacy—I&II. Degradation of Polymers," Chemical Abstracts, vol. 69, No. 20, pp. 7513, Abstract No. 80161r &No. 80162 (Nov. 11, 1968).

Parkin et al., "Atopic manifestations in the acquired immune deficiency syndrome: response to recombinant interferon gamma," 294 British Medical Journal 1185-1186 (1987).

Perry et al., Perry's Chemical Engineering Handbook (McGraw-Hill, NY 1984).

"Pharmaceutical Sciences," Chapter 19—Disperse Systems pp. 267-272 Chapter 87—Medicated Applications pp. 1600-1606, 1614 Chapter 91—Sustained-Release Drug Delivery Systems pp. 1690-1693, Mack Publishing Co, Easton PA (1990).

Pishko et al., "Amperometric Glucose Microelectrodes Prepared through Immobilization of Glucose Oxidase in Redox Hydrogels," Anal. Chem. 63:2268-2272 (1991).

Potts and Guy, "Predicting Skin Permeability," Pharm. Res. 9:663-669 (1992).

Prausnitz et al., "Electroporation of mammalian skin: A mechanism to enhance transdermal drug delivery," 90 Proc. Natl. Acad. Sci. USA 10504-10508 (Nov. 15, 1993).

W.S. Quillen, "Phonophoresis: A Review of the Literature and Technique," Athletic Training 15:109-110 (1980).

Robinson & Lee, "Influence of Drug Properties on Design," Controlled Drug Delivery 42-43.

J. Rosell et al., "Skin Impedance from 1 Hz to 1 MHz," IEEE Trans. Biomed. Eng. 35:649-651 (1988).

Schreier & Bouwstra, "Liposomes and noisomes as topical drug carriers: dermal and transdermal drug delivery," 30 Journal of Controlled Release 1-15 (1994).

Skauen & Zentner, "Phonophoresis," Int. J. Pharm. 20, 235-245 (1984).

Stringfellow, "Clinical Applications of Interferons and Their Inducers," (Marcel Dekker ed., 2d ed. 1986).

Tamada et al., "Correlation of Blood Glucose With Iontophoretic Glucose Flux in Human Subjects for Glucose Monitoring," Proceed. Intern. Symp. Control. Rel. Bioact. Mater. 22, 129-130 (1995).

Tang, H. et al., "Theoretical description of transdermal transport of hydrophilic permeants: application to low-frequency sonophoresis," 90 J. Pharmaceutical Sciences 545-568 (Mar. 28, 2001).

A. Tezel et al., "Synergistic Effect of Low-Frequency Ultrasound and Surfactants on Skin Permeability," J. Pharmaceutical Sciences, vol. 91, No. 1, pp. 91-100 (Jan. 2002).

Tocanne et al., "Lipid lateral diffusion and membrane organization," FEBS Letters, vol. 257, pp. 10-16 (1989).

Tyle and Agrawala, "Drug Delivery by Phonophoresis," Pharm. Res. 6:355-361 (1989).

Michel M. Veillard et al., "Buccal Controlled Delivery of Peptides," 14 Proceed. Intern. Symp. Control. Rel. Bioact. Mater 22 (Controlled Release Society, Inc. 1987).

Walker and Hadgraft, "Oleic Acid—a membrane 'fluidiser' or fluid within the membrane," Int. J. Pharm. 71:R1-R4 (1991).

Walmsley, "Applications of Ultrasound in Dentistry," Ultrasound in Med. and Biol. 14:7-14 (1988).

Walters, K.A., "Penetration Enhancers and Their Use in Transdermal Therapeutic Systems," Transdermal Drug Delivery: Developmental Issues and Research Initatives, 197-246 (Hadgraft et al. eds. 1989).

Wester and Mailbach, "Animal Models for Percutaneous Absorption," Topical Drug Bioavailability Bioequivalence and Penetration 333-349 (1993).

Wheatley et al., "Use of Ussing Chamber for Investigation of Drug Delivery Across Viable Nasal Tissue Membranes," 14 Proceed. Intern. Symp. Rel. Bioact. Mater. 26-27 (Controlled Release Society, Inc. 1987).

Williams et al., "On the non-Gaussian distribution of human skin permeabilities," 86 Int. J. Pharm. 69-77 (1992).

Wilschut et al., "Estimating Skin Permeation. The Validation of Five Mathematical Skin Permeation Models," Chemosphere 30:1275-1296 (1995).

U.S. Appl. No. 09/868,442, filed Dec. 17, 1999, Samir Mitragotri et al.

* cited by examiner

METHOD AND APPARATUS FOR ENHANCEMENT OF TRANSDERMAL TRANSPORT

RELATED APPLICATIONS

This application is a Divisional of U.S. patent application Ser. No. 09/686,442, filed Jul. 24, 2001 now abandoned, entitled "METHOD AND APPARATUS FOR ENHANCEMENT OF TRANSDERMAL TRANSPORT," which is a 371 of PCT/US99/30065 filed Dec. 17, 1999, which claims priority to provisional application Nos. 60/112,953 filed Dec. 18, 1998; 60/142,941 filed Jul. 12, 1999; 60/142,950 filed Jul. 12, 1999; 60/142,951 filed Jul. 12, 1999; and 60/142,975 filed Jul. 12, 1999. This application and parent application Ser. No. 09/868,442 also claim priority to U.S. Ser. No. 09/227,623 filed Jan. 8, 1999, now U.S. Pat. No. 6,190,315 and U.S. Provisional Application No. 60/070,813 filed Jan. 8, 1998. The contents of all of the foregoing applications are incorporated herein by reference in their entirety.

BACKGROUND OF THE INVENTION

1. Field of the Invention

This invention relates to transdermal molecular transportation. More specifically, this invention relates to methods and apparatus for the regulation of skin permeabilization and analysis of analytes in extracted body fluid.

2. Description of the Related Art

Drugs are routinely administered either orally or by injection. The effectiveness of most drugs relies on achieving a certain concentration in the bloodstream. Although some drugs have inherent side effects which cannot be eliminated in any dosage form, many drugs exhibit undesirable behaviors that are specifically related to a particular route of administration. For example, drugs may be degraded in the GI tract by the low gastric pH, local enzymes or interaction with food or drink within the stomach. The drug or disease itself may forestall or compromise drug absorption because of vomiting or diarrhea. If a drug entity survives its trip through the GI tract, it may face rapid metabolism to pharmacologically inactive forms by the liver, the first-pass effect. Sometimes the drug itself has inherent undesirable attributes such as a short half-life or a narrow therapeutic blood level range.

Recently, efforts aimed at eliminating some of the problems of traditional dosage forms involve transdermal delivery of the drugs (TDD). Topical application has been used for a very long time, mostly in the treatment of localized skin diseases. Local treatments, however, only require that the drug permeate the outer layers of the skin to treat the diseased state, with little or no systemic accumulation. Transdermal delivery systems are designed for, inter alia, obtaining systemic blood levels, and topical drug application. For purposes of this application, the word "transdermal" is used as a generic term to describe the passage of substances into, out of, to, and through the skin.

TDD offers several advantages over traditional delivery methods, including injections and oral delivery. When compared to oral delivery, TDD avoids gastrointestinal drug metabolism, reduces first-pass effects, and provides sustained release of drugs for up to seven days, as reported by Elias in Percutaneous Absorption: Mechanisms-Methodology-Drug Delivery, Bronaugh, R. L. Maibach, H. I. (Ed), pp 1-12, Marcel Dekker, New York, 1989.

The transport of drugs to, into, out of, and through the skin is complex since many factors influence their permeation. These include the skin structure and its properties, the penetrating molecule and its physical-chemical relationship to the skin and the delivery matrix, and the combination of the skin, the penetrant, and the delivery system as a whole. Particularly, the skin is a complex structure. There are at least four distinct layers of tissue: the nonviable epidermis (stratum corneum, SC) the viable epidermis, the viable dermis, the subcutaneous connective tissue. Located within these layers are the skin's circulatory system, the arterial plexus, and appendages, including hair follicles, sebaceous glands, and sweat glands. The circulatory system lies in the dermis and tissues below the dermis. The capillaries do not actually enter the epidermal tissue but come within 150 to 200 microns of the outer surface of the skin.

In comparison to injections, TDD can reduce or eliminate the associated pain and the possibility of infection. Theoretically, the transdermal route of drug administration could be advantageous in the delivery of many therapeutic drugs, including proteins, because many drugs, including proteins, are susceptible to gastrointestinal degradation and exhibit poor gastrointestinal uptake. Proteins, such as interferon, are cleared rapidly from the blood and need to be delivered at a sustained rate in order to maintain their blood concentration at a high value. Transdermal devices are also easier to use than injections.

In spite of these advantages, very few drugs and no proteins or peptides are currently administered transdermally for clinical applications because of the low skin permeability to drugs. This low permeability is attributed to the SC, the outermost skin layer which consists of flat, dead cells filled with keratin fibers (keratinocytes) surrounded by lipid bilayers. The highly-ordered structure of the lipid bilayers confers an impermeable character to the SC (Flynn, G. L., in Percutaneous Absorption: Mechanisms-Methodology-Drug Delivery; Bronaugh, R. L., Maibach. H. I. (Ed). pages 27-53, Marcel Dekker, New-York 1989). Several methods have been proposed to enhance transdermal drug transport, including the use of chemical enhancers, i.e., the use of chemicals to either modify the skin structure or to increase the drug concentration in a transdermal patch (Burnette, R. R., in Developmental Issues and Research Initiatives; Hadgraf J., Guy, R. H., Eds., Marcel Dekker: 1989; pp. 247-288; Junginger, et al. in Drug Permeation Enhancement; Hsieh, D. S., Eds., pp. 59-90; Marcel Dekker, Inc. New York 1994) and the use of applications of electric fields to create transient transport pathways (electroporation) or to increase the mobility of charged drugs through the skin (iontophoresis) (Prausnitz Proc. Natl. Acad. Sci. USA 90, 10504-10508 (1993); Walters, K. A., in Transdermal Drug Delivery: Developmental Issues and Research Initiatives, Ed. Hadgraf J., Guy, R. H., Marcel. Dekker, 1989). Another approach that has been explored is the application of ultrasound.

Ultrasound has been shown to enhance transdermal transport of drugs across human skin, a phenomenon referred to as sonophoresis (Levy, J. Clin. Invest. 1989, 83, 2974-2078; Kost and Langer in "Topical drug Bioavailability, Bioequivalence, and Penetration"; pp. 9.1-103, Shah V. P., Maibach H. I., Eds. (Plenum: New York, 1993). For example, U.S. Pat. No. 4,309,989 to Fahim and U.S. Pat. No. 4,767,402 issued to Kost et al. both describe the use of ultrasound in conjunction with transdermal drug delivery. U.S. Pat. No. 4,309,989 discloses the topical application of a medication using ultrasound with a coupling agent such as oil. Ultrasound at a frequency of at least 1000 kHz and a power of one to three $W/cm^2$ was used to create selective localized intracellular concentration of a zinc-containing compound for the treatment of herpes simplex virus.

U.S. Pat. No. 4,309,989, the disclosure of which is incorporated by reference in its entirety, discloses the use of ultrasound for enhancing and controlling transdermal permeation of a molecule, including drugs, antigens, vitamins, inorganic and organic compounds, and various combinations of these substances, through the skin and into the circulatory system. Ultrasound having a frequency of about 20 kHz and having an intensity between about 0 and 3 W/cm$^2$ is used essentially to drive molecules through the skin and into the circulatory system.

Although a variety of ultrasound conditions have bee used for sonophoresis, the most commonly used conditions correspond to therapeutic ultrasound (frequency in the range of between one MHz and three MHz, and intensity in the range of between above zero and two W/cm$^2$) (such as that described in the Kost et al. patent). It is a common observation that the typical enhancement induced by therapeutic ultrasound is less than ten-fold. In many cases, no enhancement of transdermal drug transport has been observed upon ultrasound application. Accordingly, a better selection of ultrasound techniques is needed to induce a higher enhancement of transdermal drug transport by sonophoresis.

Application of low-frequency ultrasound (between about 20 and 200 kHz) can dramatically enhance transdermal transport of drugs, as well as the extraction and measurement of analyte, as described in PCT/US96/12244 by Massachusetts Institute of Technology. Transdermal transport enhancement induced by low-frequency ultrasound was found to be as much as 1000-fold higher than that induced by therapeutic ultrasound. Another advantage of low-frequency sonophoresis as compared to therapeutic ultrasound is that the former can induce transdermal transport of drugs which do not passively permeate across the skin.

Ultrasound gels may be used as couplings in most medical applications of ultrasound energy. Use of these gels may be messy and labor-intensive. To overcome problems associated with applying ultrasound with gels and other coupling agents, patches containing the required components have been developed. A patch adheres to a clean area of the skin, and drug molecules are continually absorbed through the skin into the bloodstream for systematic distribution. These patches include a drug-containing layer provided near an ultrasonic oscillator. Drug absorption is ensured by the action of the ultrasonic waves from the oscillator. The amount of drug released may be controlled by varying the ultrasonic wave output from the oscillator, as described in U.S. Pat. No. 5,007,438 to Tachibana, et al., the disclosure of which is incorporated by reference in its entirety. U.S. Pat. No. 4,821,740 to Tachibana et al. discloses a kit for providing external medicines that includes a drug containing layer and an ultrasonic oscillator for releasing the drugs for uptake through the surface of the skin. The transducer may be battery powered. The application of the ultrasound causes the medication to move from the device to the skin and then the ultrasound energy may be varied to control the rate of administration through the skin.

U.S. Pat. No. 5,421,816 to Lipkovker describes ultrasonic energy that releases a stored drug and forcibly moves the drug through the skin of an organism and to the blood stream. A housing includes a cavity defined by an assembly of ultrasonic transducers and separated from the skin by a polymeric membrane that stores the drug to be delivered. The ultrasonic transducer assembly includes a flat, circular ultrasonic transducer that defines the top of a truncated cone and a polarity of transducer segments that define the walls of the cone. The resonant frequency of the planar transducer is lower than the resonant frequency of the transducer segments. The planar, flat, circular transducer generates a fixed frequency in the 5 kHz to 1 MHz range, and ultrasonic stimuli impulses for a predetermined period of time, such as 10-20 seconds.

Between the stimuli pulse periods, the transducer segments receive variable frequency ultrasonic pumping pulses. The variable frequency ultrasonic pumping pulses lie in the 50 MHz to 300 MHz range. The variable frequency ultrasonic pumping pulses are applied to opposing transducer segments. The transducer segments create beams that impinge on the skin at an oblique angle to create a pulsating wave. Further, the variable frequency ultrasonic pumping pulses are applied to opposing transducer segments in a rotating manner to create pulsating waves in the skin in a variety of directions. The stimuli pulses cause the planar transducer to produce an ultrasonic wave that excites the local nerves in a way that trauma, such as heat and force, excites local nerves. The variable frequency ultrasonic pumping pulses cause the transducer segments to produce ultrasonic waves in both the polymeric membrane and the skin. The ultrasonic waves pump the drug to the polymeric membrane and, then, through skin openings into the underlying blood vessels.

Thus ultrasound energy may serve to enhance the flux of active permeate molecules through the skin and other biological membranes by providing an active energy source, in addition to passive diffusion, to push or pump molecules through pores and channels.

In addition to there being a need to deliver drugs through the skin, there is a major medical need to extract analytes through the skin. For example, it is desirable for diabetics to measure blood glucose several times per day in order to optimize insulin treatment and thereby reduce the severe long-term complications of the disease. Currently, diabetics do this by pricking the highly vascularized fingertips with a lancet to perforate the skin, then milking the skin with manual pressure to produce a drop of blood, which is then assayed for glucose using a disposable diagnostic strip and a meter into which this strip fits. This method of glucose measurement has the major disadvantage that it is painful, so diabetics do not like to obtain a glucose measurement as often as is medically indicated.

Therefore, many groups are working on non-invasive, and less invasive means to measure glucose, such as micro lancets that are very small in diameter, very sharp, and penetrate only to the interstitium (not to the blood vessels of the dermis). A small sample, from about 0.1 to two µl, of interstitial fluid is obtained through capillary forces for glucose measurements. Other groups have used a laser to breach the integrity of the stratum corneum and thereby make it possible for blood or interstitial fluid to diffuse out of such a hole or to be obtained through such a hole using pneumatic force (suction) or other techniques. An example of such a laser based sampling device is disclosed in U.S. Pat. No. 5,165,418 to Tankovich and WPI ACC No: 94-167045/20 by Budnik (assigned to Venisect, Inc.).

A problem with methods that penetrate the skin to obtain interstitial fluid is that interstitial fluid occurs in the body in a gel like form with little free fluid and, in fact, is even under negative pressure that limits the amount of free interstitial fluid that can be obtained. When a very small hole is made in the skin, penetrating to a depth such that interstitial fluid is available, it takes a great deal of mechanical force (milking, vacuum, or other force) to obtain the requisite quantity of blood, or interstitial fluid, used in a glucose meter.

Channeling of ultrasound geometrically is one way to apply ultrasound to a small area. Channeling of ultrasound is disclosed in PCT Patent Application No. PCT/US97/11559 entitled "Ultrasound Enhancement of Transdermal Transport" by Sontra L. P. et al., filed Jun. 30, 1997, and incorporated by reference in its entirety. The oscillation of a small element near or in contact with the surface of the skin is another way to apply ultrasound to a small area. Large forces can be produced locally, resulting in cavitation, mechanical oscillations in the skin itself, and large localized shearing forces near the surface of the skin. The element can also produce acoustic streaming, which refers to the large convective flows produced by ultrasound. This appears to aid in obtaining a sample of blood or interstitial fluid without having to "milk" the puncture site. Ultrasound transducers are known to rapidly heat under continuous operation, reaching temperatures that can cause skin damage. Heat damage to the skin can be minimized by using a transducer that is located away from the skin to oscillate a small element near the skin. In the case of analyte extraction, compounds present on the surface of and/or in the skin can contaminate the extracted sample. The level of contamination increases as skin surface area increases. Surface contamination can be minimized by minimizing the surface area of ultrasound application. Thus, skin permeability can be increased locally, and transiently through the use of the methods and devices described herein, for either drug delivery or measurement of analyte.

Moreover, it has been disclosed that the application of ultrasound is only required once for multiple deliveries or extractions over an extended period of time rather than prior to each extraction or delivery. That is, it has been shown that if ultrasound having a particular frequency and a particular intensity is applied, multiple analyte extractions or drug deliveries may be performed over an extended period of time. For example, if ultrasound having a frequency of 20 kHz and an intensity of about 10 W/cm$^2$ is applied, the skin retains an increased permeability for a period of up to four hours. This is described more particularly in U.S. patent application Ser. No. 09/227,623 entitled "Sonophoretic Enhanced Transdermal Transport" by Mitragotri et al., filed on Jan. 8, 1999, and in PCT Application No. PCT/US99/00437 entitled "Sonophoretic Enhanced. Transdermal Transport" by Sontra Medical et al., filed Jan. 8, 1999 the disclosures of which are hereby incorporated by reference in their entireties.

Nevertheless, the amount (e.g., duration, intensity, duty cycle etc.) of ultrasound necessary to achieve this permeability enhancement varies widely. Several factors of the nature of skin must be considered. For example, the type of skin which the substance is to pass through varies from species to species, varies according to age (e.g., the skin of an infant has a greater permeability than that of an older adult), varies according to local composition, thickness and density, varies as a function of injury or exposure to agents such as organic solvents or surfactants, and varies as a function of some diseases, such as psoriasis, or abrasion. Moreover, as discussed above, overexposure to ultrasound and cavitation can cause damage to the skin through heating and increased pressure. Therefore, it is necessary to control the ultrasound application in order to enable clinically useful transdermal transport.

SUMMARY OF THE INVENTION

Therefore, a need has arisen for a method and apparatus for regulation of skin permeabilization through a feedback system.

A need has arisen for a method and apparatus that provides controlled enhancement of transdermal transport.

A need has also arisen for a system and method for extraction and analysis of at least one analyte in a body fluid.

A need has also arisen for a method and apparatus for sonophoretic drug delivery.

According to the present invention, a method for enhancing transdermal transport is disclosed. The method includes the steps of increasing a permeability of an area of a membrane with a permeabilizing device. Next, the permeability of the area of membrane is monitored. A substance is transported into and through the area of the membrane.

According to one embodiment of the present invention, a method for enhancing permeability of an area of skin is disclosed. The method comprises applying ultrasound to the area of skin. While the ultrasound is being applied, electricity (e.g., an ac current source or an ac voltage source) is applied to the area of skin. While the electricity is being applied to the area of skin, a first electrical parameter of the area of skin is measured. Based on the measured first electrical parameter, the ultrasound is controlled.

According to another embodiment, the present invention comprises an apparatus for enhancing the permeability of an area of skin. The apparatus includes an ultrasound-producing device configured to apply ultrasound to the area of skin, an electrical source operable to apply electricity to the area of skin, a circuit to measure a first electrical parameter of the area of skin, and a controller responsive to the circuit and operable to control the ultrasound-producing device.

According to another embodiment, the present invention comprises a method for enhancing the permeability of an area of skin. The method begins by creating a volume of fluid adjacent the area of skin. The fluid has an initial concentration of a first substance. Ultrasound is then applied to the area of skin. While the ultrasound is being applied, changes in the concentration of the first substance are monitored. Finally, the method controls the ultrasound based on the changes in the concentration of the substance.

According to another embodiment, the present invention comprises a method for enhancing the permeability of an area of skin. The method begins by creating a volume of fluid adjacent the area of skin whose permeability is to be enhanced. A reference value for an electrical parameter of the volume of fluid is then determined. The method then applies ultrasound to the area of skin and monitors changes in the electrical parameter of the volume of fluid. Finally, the ultrasound is controlled based on the changes in the electrical parameter of the volume of fluid.

According to another embodiment of the present invention, a method for regulating skin permeabilization is disclosed. The method comprises coupling a first electrode in electrical contact with a first area of skin. A second electrode is placed in electrical contact with a second area of skin. The initial conductivity between these sites is measured, and then a skin permeabilizing method, such as ultrasound, is applied to the first area of skin. The conductivity between the first area and second area is measured again. Mathematical analysis or signal processing is performed on the conductivity information Next parameters describing the kinetics of skin conductance are calculated. Next, once the desired value of the parameters are reached, the skin permeabilizing step is terminated.

According to another embodiment, the present invention comprises an apparatus for enhancing permeability of an area of skin. The apparatus includes a first electrode for coupling in electrical contact with a first area of skin, and a second electrode for placement in electrical contact with a second area of skin. A skin permeabilizing device, such as an ultrasound-producing device, is provided to apply a skin permeabilizing treatment to the skin at the first area. A means for measuring the conductivity between the first area and second area are provided. A controller, for performing mathematical analysis or signal processing on the conductivity information, and for calculating the kinetics of skin conductance is provided. The controller also controls the skin permeabilizing device.

According to another embodiment of the present invention, a method for extraction and analysis of at least one analyte in a body fluid is disclosed. According to this method, first the permeability level of an area of skin is increased. Next, a body fluid is extracted from the area of skin. Then, the body fluid is collected. Next, a determination is made as to the presence of at least one analyte in the body fluid.

The body fluid may be extracted by physical forces, chemical forces, biological forces, vacuum pressure, electrical forces, osmotic forces, diffusion forces, electromagnetic forces, ultrasound forces, cavitation forces, mechanical forces, thermal forces, capillary forces, fluid circulation across the skin, electro-acoustic forces, magnetic forces, magneto-hydrodynamic forces, acoustic forces, convective dispersion, photo acoustic forces, by rinsing body fluid off skin, and any combination thereof. The body fluid may be collected by a collection method including absorption, adsorption, phase separation, mechanical, electrical, chemically induced, and a combination thereof. The presence of an analyte may be sensed by a sensing method including electrochemical, optical, acoustical, biological, enzymatic technology, and combinations thereof.

According to another embodiment of the present invention, a system for extraction and analysis of at least one analyte in a body fluid is disclosed. The system comprises a transducer for increasing the permeability of an area of skin; an extraction device for extracting interstitial fluid from the area of skin; a collection device for collecting the extracted interstitial fluid; and a sensing device for sensing the presence of at least one analyte in the extracted interstitial fluid.

According, to another embodiment of the present invention, a method for blood glucose determination is disclosed. The method includes first increasing a permeability of an area of skin. Next, interstitial fluid, or components thereof, is extracted from the area of skin. In another embodiment, the interstitial fluid, or components thereof, diffuse through the skin, and are collected. Next, the interstitial fluid is collected in a gel. The gel may contain at least one glucose sensitive reagent that changes at least one characteristic of the gel, such as color, when glucose is present. Finally, the change in the characteristic of the gel is monitored.

According to another embodiment of the present invention, a system for blood glucose determination is disclosed. The system comprises a transducer for increasing the permeability of the skin; an extraction device for extracting interstitial fluid from the skin; a collection device for collecting the extracted interstitial fluid; a gel having at least one glucose sensitive reagent that changes a characteristic of the gel when glucose is present; and a monitoring device for monitoring a change in the characteristic of said gel.

According to another embodiment of the present invention, a drug delivery patch apparatus is disclosed. The apparatus includes an ultrasound transducer for applying ultrasound to a membrane. The membrane may include biological membranes, synthetic membranes, or a cell culture. A biological membrane may include skin, mucosal and buccal membranes. The apparatus further includes a power source coupled to the transducer. The apparatus further includes drug molecules between the transducer and the membrane, and an attaching device that attaches the apparatus to the membrane. According to another embodiment, the apparatus further includes drive electronics coupled to the transducer such that the drive electronics enables the transducer to apply ultrasound. According to another embodiment, the apparatus further includes an interface coupled to the drive electronics.

The drug delivery patch apparatus may include the interface, drive electronics, power source, transducer, drug molecules, and attaching device contained within the patch for transdermal delivery through the membrane. Alternatively, the transducer and the drug molecules as well as the attaching device may be contained in the patch. The power source and interface may be connected to the patch with a connecting wire, or without a wire. Alternatively, the drug delivery patch may include the power source, the transducer, the drug molecules and the attaching device within the patch. The interface may be located elsewhere and communicates to the patch through hardwires, infrared, fiber optics, or telemetry.

According to another embodiment of the present invention, a method for transdermal vaccination by sonophoresis is disclosed. According to the one embodiment, the method comprises the steps of enhancing the permeability of the skin by the application of ultrasound; providing a vaccine to the permeabilized skin; and delivering the vaccine to the skin cells, for example, Langerhans cells, dendric cells, and keratinocytes.

In another embodiment of the present invention, ultrasound is used to enhance the permeability of the skin. In another embodiment of the present invention, the steps of increasing the permeability of the skin and providing a vaccine to the permeabilized skin occur simultaneously.

In another embodiment of the present invention, ultrasound is used to irritate or inflame an area of skin. Next, a vaccine is provided to the irritated or inflamed skin. This is more effective in inducing the immune response of the body.

BRIEF DESCRIPTION OF THE DRAWINGS

The features and objects of the present invention, and the manner of attaining them is explained in detail in the following DETAILED DESCRIPTION OF THE PREFERRED EMBODIMENTS of the invention when taken in conjunction with the accompanying drawings wherein.

DETAILED DESCRIPTION OF THE PREFERRED EMBODIMENTS

As used herein, the terms skin permeabilizing method or device includes the application of ultrasound, chemicals, electroporation, mechanical, disrupting devices, tape stripping, and, laser, and devices for the application of the same. In addition, the term skin includes membranes, such as biologic and synthetic skin.

Ultrasound is generally defined as sound at a frequency of greater than about 20 kHz. Therapeutic ultrasound is typically between 20 kHz and 5 MHz. Sonophoresis is defined as the application of ultrasound to the skin resulting in enhanced transdermal transport of molecules. Low frequency sonophoresis or ultrasound is defined as sonophoresis or ultrasound at a frequency that is less than 2.5 MHz, more typically less than 1 MHz, more preferably in the range of 20 to 100 kHz.

Near ultrasound is typically about 10 kHz to 20 kHz. It should be understood that in addition to ultrasound, near ultrasound may also be used in the embodiments of the present invention.

1. Enhancement and Regulation of Skin Permeability

The use of ultrasound to facilitate transdermal transport is known. The mechanism by which ultrasound is used to facilitate transdermal transport has differed. In the context of transdermal delivery systems, ultrasound was initially used as a driving force that essentially pushed drugs through the skin and into the circulatory system. Ultrasound is also used to increase the permeability of the skin. That is, application of ultrasound having a particular frequency will disorganize the lipid bilayer in the skin and thus increase the permeability of the skin. In this context, either drugs can be delivered through the skin to the body or analyte or analytes can be extracted through the skin from the body. A driving force of some type is still required, but the required intensity of the driving force is decreased. For example, a concentration gradient is generally sufficient driving force for transdermal transport through skin whose permeability has been enhanced using ultrasound.

Figure 1:
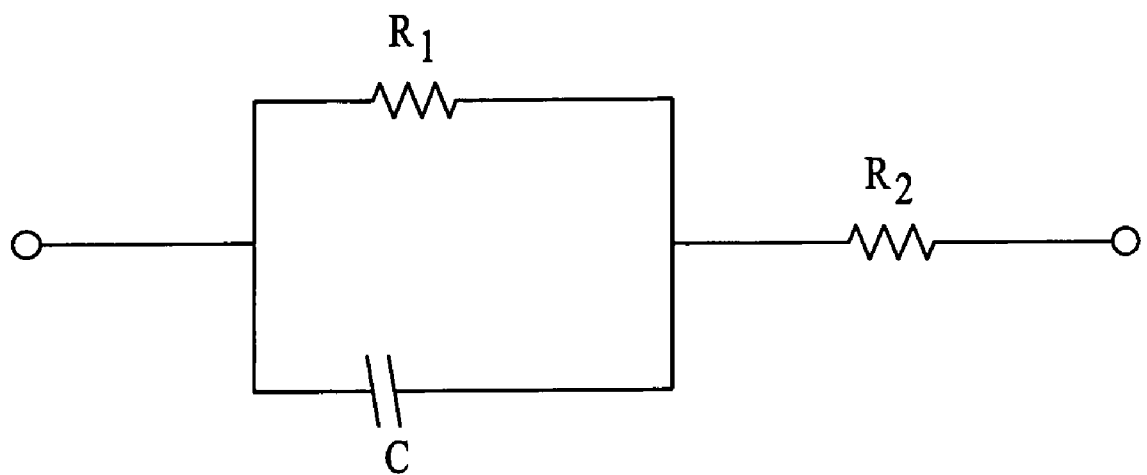
FIG. 1 depicts a schematic of an electrical model for skin.

Regardless of which mechanism is used, the ultrasound still needs to be controlled. That is, overexposure to ultrasound may cause skin damage from increased heat, increased pressure and other factors. Therefore according to various embodiments of the present invention, a method and an apparatus for controlled enhancement of skin permeability are disclosed. The method and apparatus, according to the present invention, focus on the use of electrical parameters of the skin as a proxy for skin permeability. The skin can be modeled using an R-C circuit similar to that shown in FIG. 1. The "skin circuit," shown in FIG. 1, consists of a resistor $R_1$ in parallel with a capacitor C, both of which are in series with a resistor $R_2$. For normal, intact skin, of an area of about 1.7 $cm^2$, the value for $R_1$ is about 100 kΩ, the value for C is about 13 μF and the value for $R_2$, is about 2 kΩ. Of course, these values will vary from person to person depending on skin type and condition. By its nature, the behavior (i.e., the frequency response) of the "skin circuit" changes in response to excitations having different frequencies. For example, under normal conditions, the impedance of this circuit will decline sharply as frequency increases, for example, from 10 Hz to 1 kHz. That is, at low frequencies, the capacitive component to the impedance of the parallel combination of $R_1$ and C is significant and therefore the overall impedance of the circuit is high. At higher frequencies, however, the capacitive component to the impedance of the parallel combination decreases and, therefore, the overall impedance of the "skin circuit" declines.

Various electrical parameters of the skin (e.g., impedance, conductance, inductance and capacitance) have values that correlate with skin permeability. For example, in the circuit of FIG. 1, the value of $R_1$ significantly decreases as the skin becomes permeable. For example, $R_1$ may drop to a value around 5 kΩ for a skin area of about 1.7 $cm^2$. Therefore, the frequency response of the overall skin circuit becomes much flatter as frequency increases. That is, the difference between the impedance of the circuit at 10 Hz and 1 kHz would not be nearly as significant as at. 10 Hz alone. Thus, the methods and apparatus of the present invention measure one or more electrical parameters of an area of skin that is being exposed to ultrasound and then adjust the source of ultrasound based on the measured parameters.

Figure 2:
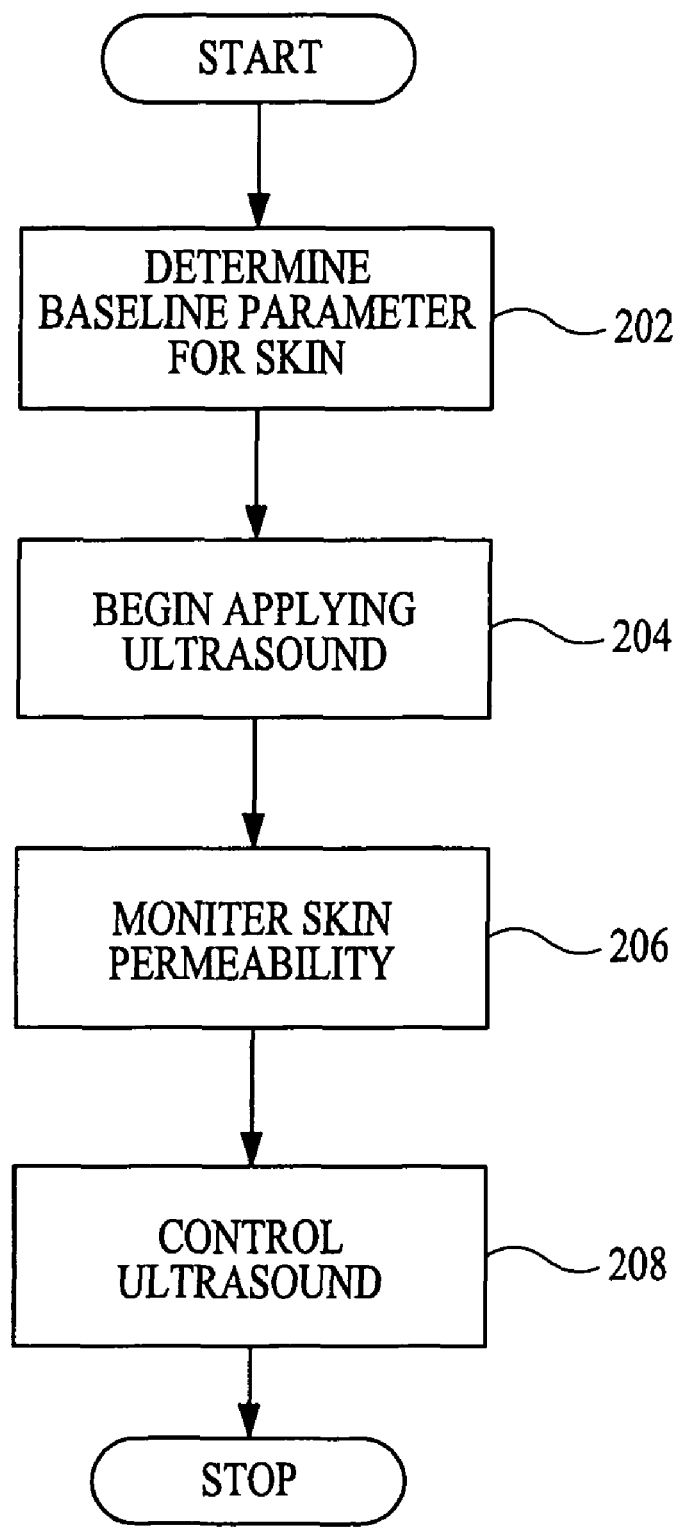
FIG. 2 depicts a flow chart of a method for controlled enhancement of transdermal delivery according to one embodiment of the present invention.

According to one embodiment of the present invention, a method for controlled enhancement of skin permeability is disclosed, and will be explained in conjunction with FIG. 2. Typically, when a skin permeabilizing device, such as an ultrasonic device, is used to enhance transdermal transport properties, the skin permeabilizing device is applied to a small patch of skin. In step 202, a baseline measurement for some electrical parameter is determined for the patch of skin to which the skin permeabilizing will be applied to determine baseline parameters. In one embodiment, a baseline impedance is measured for the patch of skin to which the skin permeabilization device is to be applied. In other embodiments, a baseline conductance, a baseline capacitance, a baseline inductance, or a baseline capacitance may be measured.

The baseline measurement may be made by using two or more electrodes. As is shown in greater detail in FIG. 3, an electrode, such as source electrode 310, is coupled to the patch of skin to which ultrasound is to be applied. Source electrode 310 does not have to make direct contact with the skin. Rather, it may be electrically coupled to the skin through the medium that is being used to transmit ultrasound. A second or counter electrode, such as conductive band 312, may be positioned on a second area of skin that the skin permeabilizing device will not be applied to. This second area of skin can be adjacent to the patch of skin to which the skin permeabilizing device will be applied, or it can be distant from that patch of skin.

In one embodiment, the ultrasonic transducer and horn that apply the ultrasound double as the source electrode through which electrical parameters of the patch of skin may be measured, and is coupled to the skin through a conductive solution, such as saline, used as an ultrasound medium. In another embodiment, a separate electrode may be affixed to the area of skin that ultrasound will be applied to and is used as the source electrode. In still another embodiment, the housing of the device used to apply ultrasound to the area of skin may be used as the source electrode. The electrode can be made of any suitable conducting material including, for example, metals and conducting polymers.

In order to achieve an accurate electrical reading, the counter electrode should make sufficient contact with the skin. This can be achieved in a number of ways. In one embodiment, the counter electrode is applied directly to the epidermis of the skin. That is, the counter electrode is applied to an area of skin from which the stratum corneum has been removed. The stratum corneum may be removed in a number of ways. According to one embodiment, the stratum corneum is removed by tape stripping. In one embodiment, sufficient electrical contact between the skin and the counter electrode is created by using a counter electrode having a large surface area. More specifically, a conductive polymeric path or metallic foil patch having an area much larger than the skin area exposed to ultrasound is used. The large area of the counter electrode in this embodiment decreases its impedance and allows accurate measurements of the electrical parameter of the area of skin exposed to ultrasound. In one specific embodiment a conductive band is wrapped around the subject's arm and used as the counter electrode. In another embodiment, the counter electrode may be placed in a handle of the skin permeabilizing device, to which a subject grasps during operation.

In another embodiment, the counter electrode surrounds the skin permeabilizing device.

When the two electrodes are properly positioned, the baseline measurement may be made by applying an electrical signal to the patch of skin through the electrodes. The electrical signal supplied preferably has a sufficient intensity so that the electrical parameter of the skin can be measured, but a suitably low intensity so that the electrical signal does not cause damage to the skin or any significant electrophoresis effect for the substance being delivered. In one embodiment, a 10 Hz AC source may be used to create a voltage differential between the source electrode and the counter electrode. In one embodiment, in order to avoid a risk of permanent damage to the skin, the voltage supplied does not exceed 500 mV, and, preferably, does not exceed 100 mV. In another embodiment, an AC current source is used. The current source may also be similarly limited. The baseline measurement is made after the source has been applied using appropriate circuitry. In one embodiment, a resistive sensor is used to measure the impedance of the patch of skin at 10 Hz. In another embodiment, a 1 kHz source is used. Sources of other frequencies are also possible.

Experiments were performed on human volunteers to ensure that the above described electrode placement would provide accurate measurements. A first glass chamber (~1.5 $cm^2$ in area) was placed on the forearm and was secured in place with an elastic strap. This first chamber was filled with 2 ml of 1% sodium lauryl sulfate (SLS) in saline. An ultrasound horn was place within the chamber and used to apply ultrasound to the skin. Additionally, an electrode used to measure electrical parameters was incorporated into the horn.

A second small chamber (~1.5 $cm^2$) was placed on the subject's arm in order to measure skin conductivity. This is referred to as the reference chamber. The skin under the reference chamber was tape-stripped using scotch tape to remove the stratum corneum. This process involved placing a piece of scotch tape (1.5 cm wide and 3 cm long) on the subject's arm and removing it. This procedure is repeated ~25 times in order to remove the stratum corneum from the designated area. An electrode was then placed on the skin under the chamber.

Another electrode is placed on the subject's arm. This electrode consisted of a large piece of aluminum foil placed on intact skin. Ultrasound (27 kHz, ~10 µm tip displacement, pulsed: 5 sec. on/5 sec. off) was applied to the first chamber. The conductance of the skin exposed to ultrasound was measured with both counter electrodes (tape stripped and intact). The measured conductances were similar thus proving that a large counter electrode placed over intact skin can be successfully used to measure skin conductance during sonophoresis.

Referring again to FIG. 2, in step 204, the skin permeabilizing device, such as an ultrasound providing device, is applied to the patch of skin. Although the exact ultrasound parameters are not the subject of this invention, according to one embodiment using an ultrasonic device as a skin permeabilizing device, ultrasound having a frequency of about 20 kHz, and an intensity of about 10 $W/cm^2$ may be used to enhance the permeability of the patch of skin to be used for transdermal transport.

After the skin permeabilizing device has been turned on, in step 206 the permeability of the patch of skin is monitored. More specifically, and as discussed above, electrical parameters of the patch of skin are used as a proxy for skin permeability. That is, what is actually being monitored is the electrical parameter for which a baseline measurement was made in step 202. The monitoring measurements are made using the same electrode set up that was used to make the baseline measurement.

In step 208, the skin permeabilizing device is controlled based on the monitoring measurements made in step 206. In one embodiment, the monitoring measurements are fed back to a microcontroller that is used to control the skin permeabilizing device. When ultrasound is used, the permeability enhancement obtained by supplying ultrasound is limited. That is, once a certain permeability is reached, the further application of ultrasound will not further enhance skin permeability. Overexposure to ultrasound, or cavitation caused thereby, may result in damage to the skin from localized pressure, temperature increases, and shear stresses. Therefore, in one embodiment, when the parameter being monitored reaches is predetermined value, the ultrasound-producing device is turned off. If the parameter being monitored has not reached the predetermined value, the measurement is repeated until the predetermined value is reached.

The predetermined value may depend upon a number of factors including, inter alia, the skin characteristics of the individual, the drug to be delivered or the analyte or analytes to be extracted (because of varying molecule sizes), and the frequency of the excitation source. As is apparent to one of ordinary skill in the art, a specific correlation between the electrical parameter being used and skin permeability may be determined by conducting experiments and using experimental data. The predetermined value may then be determined on a subject-by-subject basis, taking into account all appropriate factors and the empirical data.

According to another embodiment, the intensity of the skin permeabilizing device may be gradually scaled back as the point of maximum permeability enhancement is approached. In one embodiment, as the parameter being monitored reaches 50% of the predetermined value, either the intensity or the duty cycle may be reduced by a predetermined amount, such as 50%. This is done so that the predetermined value is not "overshot," thereby increasing the risk of skin damage. Additional controls are possible. For example, in another embodiment, the intensity may be scaled back when the parameter being monitored reaches 25%, 50% and 75% of the predetermined value.

According to another embodiment, permeability enhancement control may be accomplished using two electrical sources having different frequencies. This method relies on the observation, discussed above, that as the skin becomes more permeable, the frequency response of the skin becomes flatter. In this embodiment, the initial step 202 of measuring a baseline for the parameter is unnecessary because the ultrasound control is based on a differential between the parameter value at two different frequencies of excitation. Nevertheless, a baseline measurement may still be desirable in order to determine the range of values to expect. In this embodiment, the electrode arrangement may be the same as that described above. And, step 204 of beginning ultrasound application is also the same as recited above. Thus, the details of these steps will not be reiterated.

After the skin permeabilizing has begun, in step 206, skin permeability is monitored. In this embodiment, skin permeability is also monitored using an electrical parameter measured from the skin as a proxy. This embodiment differs from the first embodiment in that the electrical parameter is measured at two frequencies. In one embodiment, the impedance of the skin is measured at frequencies of 10 Hz and 1 kHz. These measurements are then used to control the skin permeabilizing device.

According to this embodiment, in step 208 the parameter measurement at a first frequency is compared with the parameter measurement at a second frequency to determine whether the two measurements are within a predetermined differential. If the two values are within a predetermined differential, it provides an indication that the frequency response of the skin has flattened and, therefore, is an indication that the skin has reached an enhanced level of permeability. At this point, the skin permeabilizing device is turned off. In one particular embodiment, an impedance of the skin is measured at 10 Hz and at 1 kHz. And, if the two impedance measurements are within 20% of each other, the skin permeabilizing device may be turned off.

The rate of change in the parameter measurements may also be used to determine a point at which the skin permeabilizing device is scaled back or discontinued. The rate of change of one, or both, or the parameters may be used. In another embodiment, the rate of change of the difference between the two parameters may also be used. As the rate of change reaches a predetermined value, the intensity of the skin permeabilizing device may be gradually scaled back or discontinued, in a manner similar to that discussed above.

As discussed above, the predetermined differential value may depend upon a number of factors, including, inter alia, the skin characteristics of the individual, the drug to be delivered or the analyte to be extracted (because of varying molecule sizes), and the frequencies of the exciting sources. Therefore, the predetermined differential is determined on a subject-by-subject basis taking into account all appropriate factors. Empirical data may be used to determine a precise value for the predetermined differential.

In a modification of this embodiment, the intensity of the skin permeabilizing device may be gradually scaled back as the point of maximum permeability enhancement is approached. For example, as the differential between the two parameter measurements approaches 50% of the predetermined differential value, either the intensity or the duty cycle may be reduced by a predetermined amount, such as 50%. Additional controls are possible. For example, in another embodiment, the intensity is scaled back when the differential between the two parameters being monitored reaches 25%, 50% and 75% of the predetermined differential value.

In vitro experiments were performed to assess the above two source method. Pig skin was mounted on diffusion cells. Skin was mounted on the diffusion cell and was exposed to ultrasound using 1% Sodium Lauryl Sulfate and saline solution as a coupling medium. Skin conductance was measured by placing two electrodes across the skin. The impedances were measured at two frequencies: 10 Hz and 1 kHz. The impedances measured at the frequencies differed by about 25 fold prior to application of ultrasound when the skin was not permeable. Upon sonication, the difference between the impedances at two frequencies decreased. The decrease in the differential impedance increased with time. When the skin was highly permeable, the impedances at two frequencies differed only by ~20%. Thus the difference between the impedances measured at two frequencies may be used to determine the level of permeabilization and stop sonication.

The methods described above use a single electrical parameter to control the ultrasound-producing device. Nevertheless, control of the ultrasound-producing device may also be based on two or more electrical parameters.

Figure 3A:
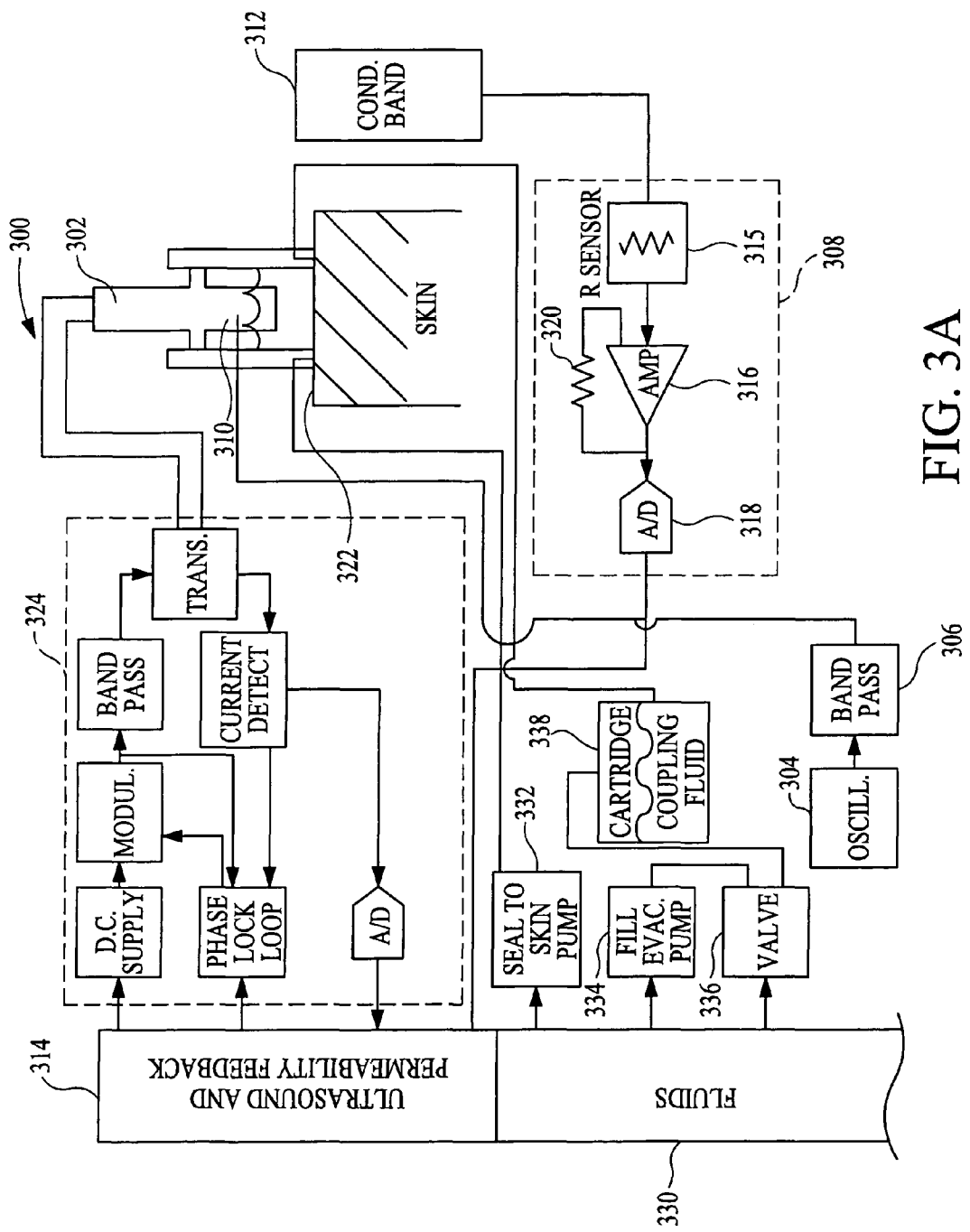
FIG. 3 depicts a diagram of a circuit that enhances skin permeability and monitors enhancement of skin permeability according to one embodiment of the present invention.
Figure 3B:
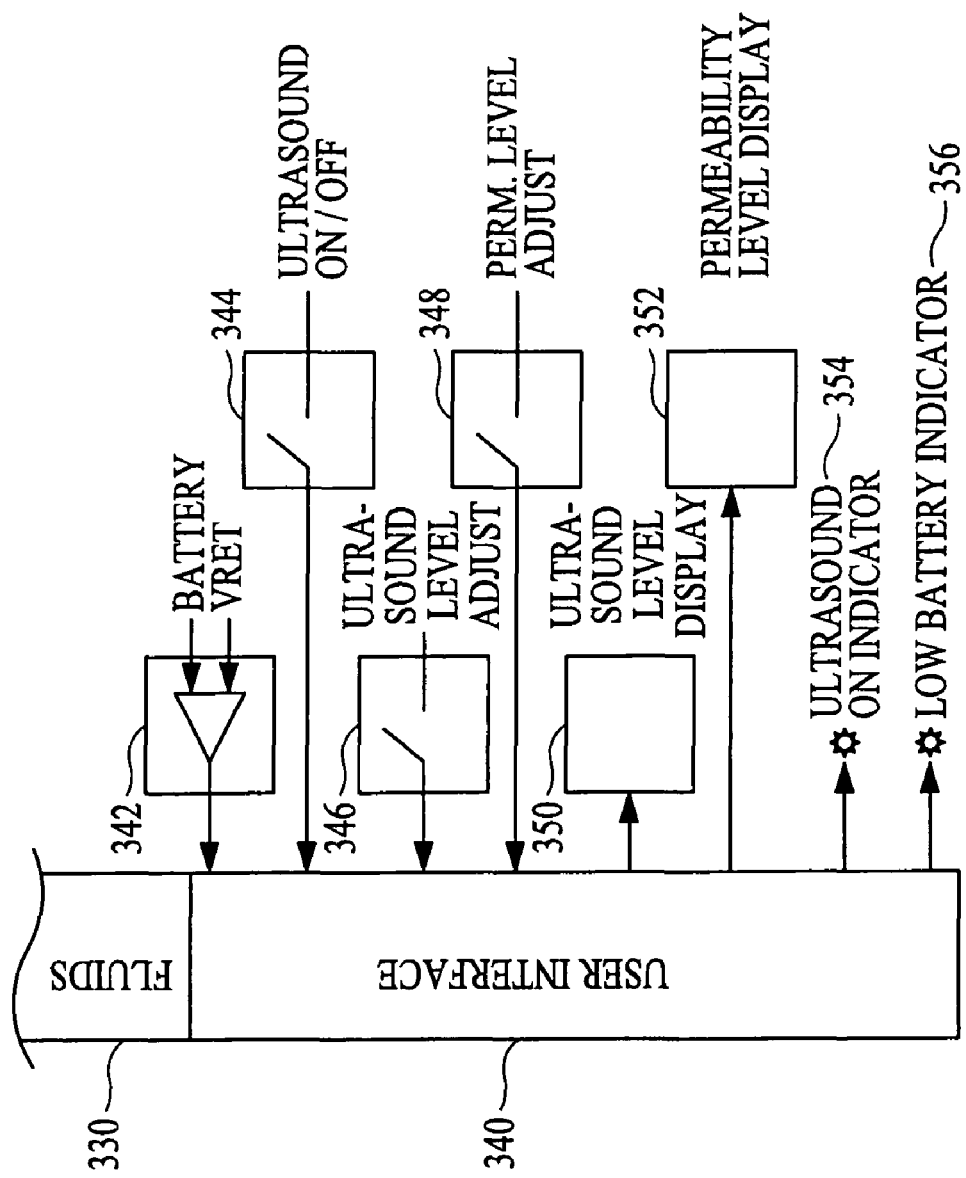

According to another embodiment of the present invention, an apparatus for controlled enhancement of transdermal transport 300 is described in conjunction with FIG. 3. Apparatus 300 uses an ultrasound-producing device as the skin permeabilizing device; it should be noted that other devices for increasing the skin permeability may be used in place of the ultrasound-producing device. For example, the permeability of the skin may be increased through the application of electric fields, chemicals, mechanical forces, needles, and magnetic forces.

Apparatus 300 includes ultrasound transducer/horn combination 302, source 304, bandpass filter 306, permeability monitoring circuit 308, source electrode 310, return electrode 312, and microcontroller 314. Permeability monitoring circuit 308 comprises current sensor 315, amplifier 316, A/D converter 318 and resistor 320.

Ultrasound transducer/horn combination 302 is used to apply ultrasound to the area of skin 322. Transducer 302 may be any known ultrasound transducer, such as a piezoelectric transducer, a ceramic transducer, or polymer block transducer. The horn can have any known configuration. In one embodiment the horn is made of a conductive metal.

As described above, while the ultrasound is being supplied to the area of skin, it is important to monitor the skin permeability and control the ultrasound application so that the skin will not be overexposed to ultrasound. Apparatus 300 may include the electrical control circuitry elements described above in order to accomplish this monitoring and control. Specifically, source 304 and bandpass filter 306 are provided to drive the electrical control circuitry. That is, in order to obtain the electrical parameter measurements used for controlling source 304, a small signal is passed through the area of skin. In one embodiment of the present invention, source 304 provides a 10 Hz AC square wave voltage that is used to monitor the permeability of the area of skin in apparatus 300. Bandpass filter 306 is provided to convert the square wave into a sinusoid.

Source electrode 310 and return electrode 312 provide an electrical path through which electrical parameters of the area of skin 322 can be measured. Source electrode 310 may be incorporated into transducer/horn combination 302, and is preferably formed of any suitable conductive material. In one embodiment, the ultrasound horn is metal and is used as the source electrode. Return electrode 312 is a conductive band and is preferably formed from a conductive polymeric path or a metallic foil.

Permeability monitoring circuit 308 comprises circuitry designed to measure an electrical parameter of the skin as a proxy for the permeability of the skin. More specifically, according to one embodiment of the present invention, permeability monitoring circuit 308 comprises circuitry designed to measure the current flow through the area, of skin 322 and to convert that measurement in to a form suitable for use by microcontroller 314. Permeability monitoring circuit 308 comprises current sensor 315 that is operable to measure the impedance of area of skin 322. Current sensor 315 may be any sensor that may be used to measure current, and, in one embodiment, current sensor 315 is a 1 kΩ current sense resistor where the output voltage generated is 1000 times the current flowing through the skin. The output of current sensor 315 is an analog signal that should be digitized before it may be used by microcontroller 315. Amplifier 316 and resistor 320 serve to amplify the output voltage of current sensor 315 so that it may be digitized by A/D converter 318. A/D converter 318 may be any suitable A/D converter.

The signal from A/D converter 316 may then be provided to microcontroller 314. Microcontroller 314 may be any suitable microcontroller. Microcontroller 314 is programmed to control transducer driver circuit 324 as described above. In one embodiment, microcontroller 314 determines whether the signal from permeability monitoring circuit 308 is greater than some predetermined value. If so, microcontroller 314 may turn off the ultrasound by, for example, shutting off the D.C. supply for transducer driver circuit 324. Microcontroller 314 may also be configured to provide other controls, such as altering the duty cycle of transducer driver circuit 324 through the phase lock loop circuit.

According to one embodiment of the present invention, additional controls and a user interface may be provided. Fluids controller 330 controls the pumps and fluids for the system. Pump 332 may be provided to provide a seal between transducer 302 and the surface of skin 322. Pump 334, in conjunction with valve 336, may be used to fill and evacuate the chamber of transducer 302. The coupling fluid used in transducer 302 may be provided in cartridge 338. Other devices and methods for providing coupling fluid may also be used.

A user interface may also be provided. User interface 340 includes low battery sensor 342, which may include a comparator. Switch 344 may be provided to turn on or off the ultrasound-producing device. Input 346 may be provided to allow a user to adjust the ultrasound intensity. The ultrasound level may be provided in display 350. The permeability level of the skin may be provided in display 352. Indicators 354 and 356 may be provided to alert the user of the operation of the ultrasound, as well as a when there is a low battery. Additional controls and displays may be provided, as required, to prevent a user from applying ultrasound of a harmful intensity or duration, or to prevent ultrasound from being applied before the system is ready (i.e., before coupling fluid is provided for transducer 302, etc.).

Figure 4:
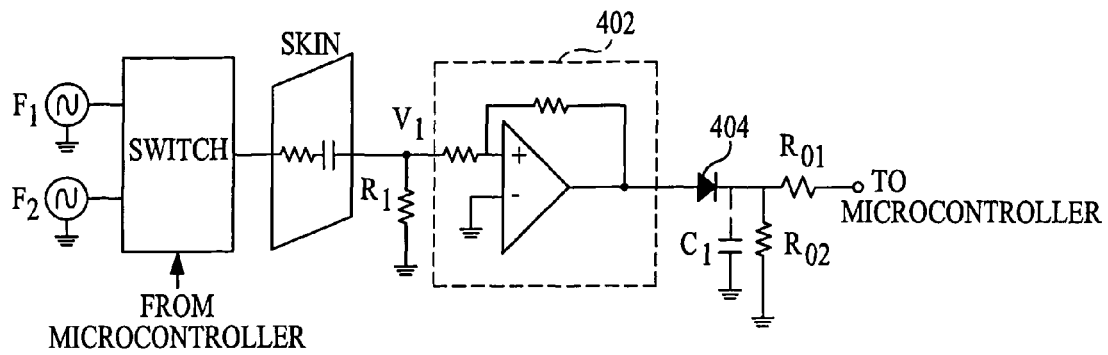
FIG. 4 depicts a permeability monitoring circuit according to another embodiment of the present invention.

The circuitry described above may be replaced with other elements if the electrical parameter measurements are accomplished in a different way. More specifically, the circuitry shown in FIG. 4 or 5 could be used in place of source 304, bandpass filter 306, and permeability monitoring circuit 308 if the control methodology using sources at two frequencies was to be used. FIG. 4 schematically depicts one embodiment of a circuit useful for implementing dual frequency control of skin permeability. The circuit comprises sources $F_1$ and $F_2$ that supply two distinct AC signals to the area of skin to which ultrasound is being applied. In one embodiment, sources $F_1$ and $F_2$ comprise a 10 Hz and a 1 kHz current source respectively. These sources are alternately applied to the area of skin through a microprocessor controlled switch. In the embodiment shown in FIG. 3, microcontroller 314 would control the switch so that sources $F_1$ and $F_2$ alternately excite the skin.

After excitation by one of the sources, the impedance of the skin is measured by measuring the voltage $V_1$. That is, $V_1$ is transmitted to a microprocessor (e.g., microcontroller 314 in FIG. 3) through gain circuit 402, diode 404, capacitor $C_1$, and output resistors $R_{O1}$ and $R_{O2}$. The combination of diode 404 and capacitor $C_1$ comprises an AC to DC converter suitable for input to an A/D converter to transform the analog signal from gain circuit 402 to a digital signal suitable for use by a microprocessor. Output resistors $R_{O1}$ and $R_{O2}$ provide impedance matching and filtering for the microprocessor, respectively.

In operation, the circuit of FIG. 4 in conjunction with a suitably programmed microcontroller alternately applies a 10 Hz and a 1 kHz AC source to the skin. The circuit, in conjunction with the microprocessor, measures the impedance of the skin at both frequencies. The microcontroller makes suitable adjustments to the ultrasound-producing device based on the differential between the impedance of the skin at 10 Hz and the impedance of the skin at 1 kHz.

Figure 5:
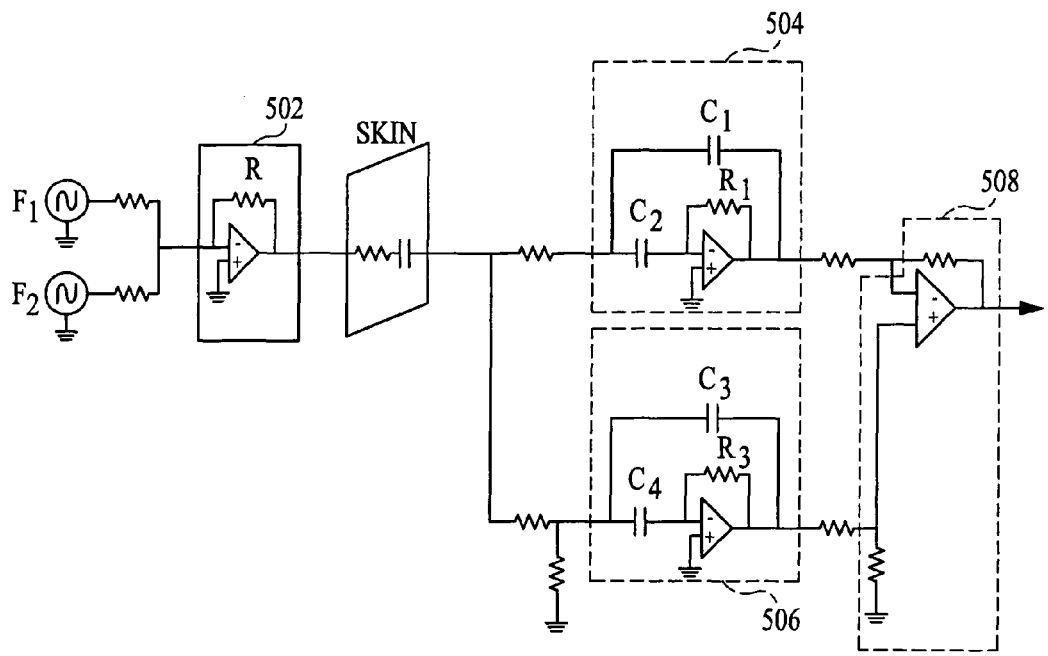
FIG. 5 depicts a permeability monitoring circuit according to one embodiment of the present invention.

FIG. 5 schematically depicts yet another embodiment of permeability monitoring circuit for use with multiple frequency excitation. In the circuit of FIG. 5, sources $F_1$ and $F_2$ are applied simultaneously through adder circuit 502 to the area of skin to which ultrasound is being applied. The output signal from the skin is then fed to two bandpass filters 504 and 506. Elements $C_1$, $C_2$ and $R_1$ of bandpass filter 504 are preferably chosen to create a pass band centered around the frequency of source $F_1$. Elements $C_3$, $C_4$ and $R_2$ of bandpass filter 506 are preferable chosen to create a pass band centered around the frequency of source $F_2$. The output signals from bandpass filters 504 and 506 are then subtracted in comparator circuit 508 to create a differential signal for the microprocessor. A suitably configured microprocessor then uses this differential signal to make suitable adjustments to the ultrasound-producing device.

Figure 6:
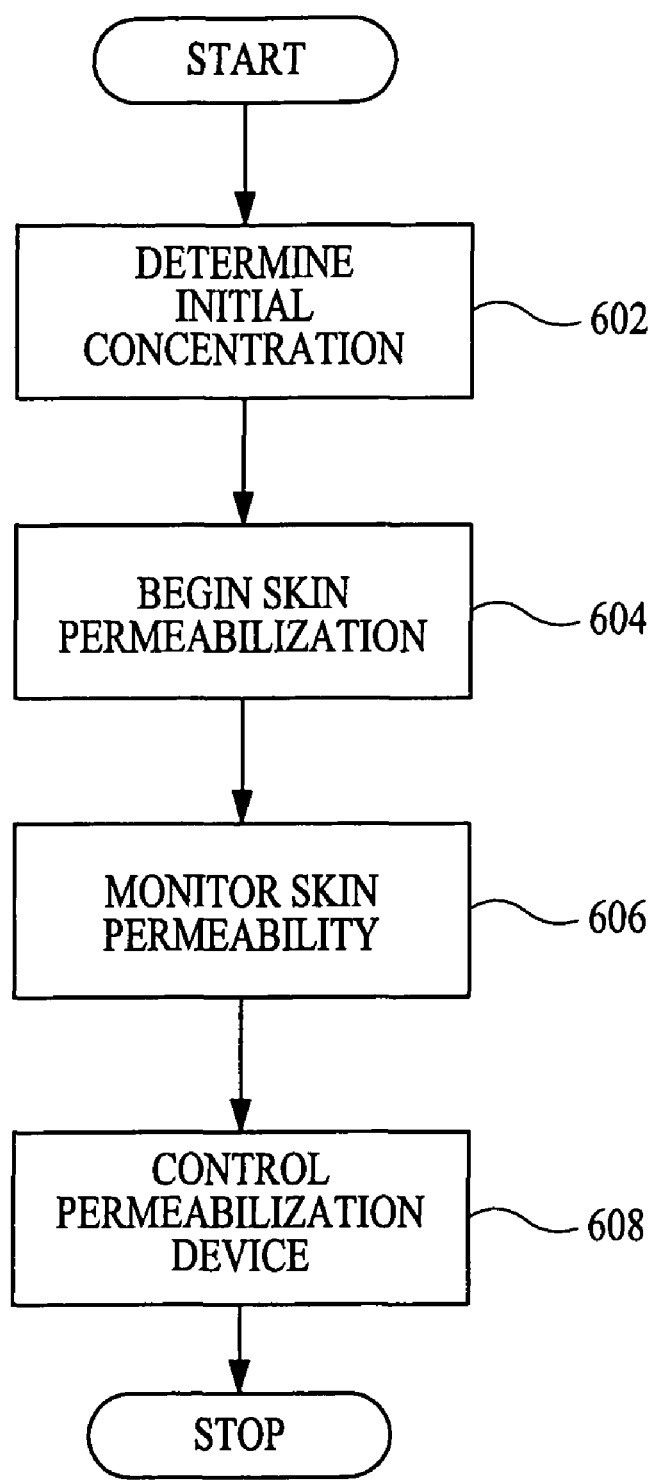
FIG. 6 depicts a flow chart of a method for controlled enhancement of transdermal delivery according to one embodiment of the present invention.

In another embodiment of the present invention, a method for controlled enhancement of skin permeability by coupling fluid monitoring is disclosed. When a skin permeabilizing device, such as an ultrasound-producing device, is applied to the skin, it is applied through some coupling fluid, which may be a liquid, gel, or solid, to facilitate transfer of the energy in the high frequency sound waves to the skin. As the skin becomes more permeable, suitably-sized molecules and ions in the coupling fluid begin to pass into and out of the skin. The method according to this embodiment takes advantage of the enhanced skin permeability that is the desired end point of this invention in order to control the skin permeabilizing device. This method will be explained in conjunction with the flow chart of FIG. 6.

In step 602 an initial concentration of a known substance is determined for the coupling medium. In practice, the coupling medium may have a known initial concentration of a known substance. That is, step 602 will not require any additional measuring. The known substance can be any substance (molecular or ionic) as long as its concentration in the coupling medium is known. If, however, the substance is going to be passed into the body, the substance should be one that is not harmful to the body. The term benign is used herein to describe such a substance. Glucose and calcium are examples of substances that may be used in this embodiment.

In step 604, the skin permeabilizing device is applied to the patch of skin. In one embodiment, an ultrasound-producing device is used as the skin permeabilizing device. Although the exact parameters of ultrasound are not the subject of this invention, according to one embodiment, ultrasound having a frequency of about 20 kHz, and an intensity of about 10 W/cm$^2$ is used to enhance the permeability of the patch of skin to be used for transdermal transport.

After the skin permeabilizing device has been turned on, in step 606 the permeability of the patch of skin is monitored. According to this embodiment, permeability monitoring is accomplished by monitoring changes in the concentration of the known substance in the coupling medium. That is, as the area of skin is subjected to the skin permeabilizing device it will become permeable. As the area of skin becomes permeable, molecules and ions begin to pass into the coupling medium from inside the body and from the coupling medium into the body depending on the concentration gradient of the substance between the body and the coupling medium. This concentration monitoring may be done in real time using an on-line sensor specifically programmed to detect and measure the concentration of the known substance.

In one embodiment, glucose is used as the known substance. The concentration of glucose is usually greater inside the body than in the coupling medium unless the concentration in the coupling medium is artificially increased. Thus, when the skin becomes permeable, glucose molecules will begin to pass into the coupling medium. In step 606, changes in the concentration of glucose in the coupling medium are monitored to determine when the skin becomes permeable.

In another embodiment, mannitol is used as the known substance. Mannitol is a benign substance as that term is used in the context of this application. The concentration of mannitol in the coupling medium is adjusted so that it is greater than the concentration of mannitol in the body. When the skin becomes permeable, mannitol molecules with begin to pass from the coupling medium into the body, decreasing the concentration of mannitol in the coupling medium. In step 606, the decrease in the concentration of mannitol in the coupling medium is monitored to determine when the skin becomes permeable.

In step 608, the skin permeabilizing device is controlled based on the concentration measurements made in step 606. In one embodiment, the concentration measurements from the chemical analyzer are fed back to a microcontroller that is used to control the skin permeabilizing device. According to another embodiment, when the concentration of the substance being monitored reaches a predetermined value, the skin permeabilizing device is turned off. If the concentration of the substance being monitored has not reached the predetermined value, the measurement is repeated until the predetermined value is reached.

The predetermined value depends upon a number of factors including, inter alia, the skin characteristics of the individual, the known substance, and the frequency of the excitation source. As is apparent to one of ordinary skill in the art, a specific correlation between the change in concentration of the known substance being used and skin permeability can be determined by conducting experiments and using experimental data. The predetermined value is then determined on a subject-by-subject basis taking into account all appropriate factors as well as any empirical data.

According to another embodiment, the intensity of the skin permeabilizing device may be gradually scaled back as the point of maximum permeability enhancement is approached. In one embodiment, where an ultrasound-producing device is used, as the concentration of the substance being monitored approaches 50% of the predetermined value, either the intensity or the duty cycle of the ultrasound may be reduced by a predetermined amount, such as 50%. This is done so that the predetermined value is not "overshot" thereby increasing the risk of skin damage. Additional controls are possible For example, in another embodiment, the intensity may be scaled back when the concentration of the substance being monitored reaches 25%, 50% and 75% of the predetermined value.

The rate of change in the concentration of the substance may also be used to determine a point at which the skin permeabilizing device is scaled back or discontinued. As the rate of change in the concentration reaches a predetermined value, the intensity of the skin permeabilizing device may be gradually scaled back or discontinued, in a manner similar to that discussed above.

Figure 7:
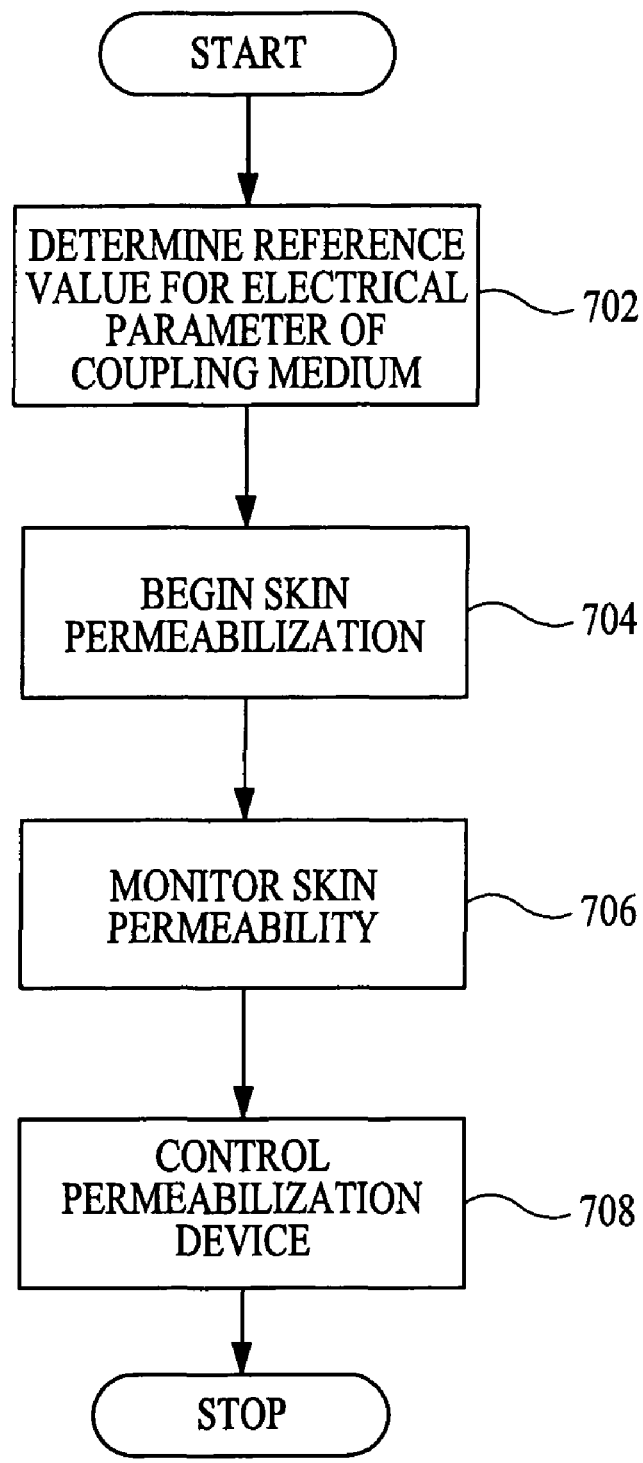
FIG. 7 depicts a flow chart of a method for controlled enhancement of transdermal delivery according to one embodiment of the present invention.

In another embodiment, skin permeability can be monitored by detecting an electrical parameter of the coupling fluid. More specifically, as skin permeability increases, ions may pass into and out of the coupling medium. As ion concentration in the coupling medium increases or decreases, the electrical characteristics of the coupling medium change. Therefore, the electrical characteristics of the coupling medium can be used to monitor skin permeability using a methodology that is a hybrid of that shown in FIGS. 2 and 6, and is set forth in FIG. 7.

In an initial step 702, a reference value for an electrical parameter is determined for the coupling medium. In practice, because the coupling medium has a known ionic composition, its electrical parameters should be known. In one embodiment, the coupling fluid has a known concentration of calcium ions. Thus, this step should not require an actual measurement. In another embodiment, the electrical parameter determined is conductivity, and in step 702, the conductivity of the coupling medium is determined.

After the reference value for the electrical parameter is determined, in step 704 the skin permeabilizing device is turned on. Then in step 706 skin permeability is determined by monitoring changes in the electrical parameter of the coupling medium. This monitoring may be accomplished using a simple meter. As the skin becomes permeable, depending upon the composition of the coupling medium, ions will pass into or out of the coupling medium and either increase or decrease the electrical parameter of the coupling medium. In one embodiment, the coupling medium has a known concentration of calcium ions that is lower than the concentration of calcium ions in the body. Therefore, as the skin becomes more permeable, calcium ions begin to pass from the body into the coupling medium.

In step 708, the skin permeabilizing device is controlled based on the monitoring measurements. In one embodiment, the monitoring measurements are fed back to a microcontroller that is used to control the skin permeabilizing device. In one embodiment, when the electrical parameter being monitored reaches is predetermined value, the skin permeabilizing device is turned off. If the parameter being monitored has not reached the predetermined value, the measurement is repeated until the predetermined value is reached.

The rate of change in the parameter being monitored may also be used to determine a point at which the skin permeabilizing device is scaled back or discontinued. As the rate of change reaches a predetermined value, the intensity of the skin permeabilizing device may be gradually scaled back or discontinued, in a manner similar to that discussed above.

The predetermined value depends upon a number of factors including, inter alia, the composition of the coupling medium, the surface area of the patch of skin to which the skin permeabilizing device is applied, and the concentration of the particular ion being used in the body. The predetermined value is determined on a subject-by-subject basis taking into account all appropriate factors and the empirical data.

According to another embodiment, the intensity of the skin permeabilizing device may be gradually scaled back as the point of maximum permeability enhancement is approached. In one embodiment, where ultrasound is used, as the parameter being monitored reaches 50% of the predetermined value, either the intensity or the duty cycle is reduced by a predetermined amount, such as 50%. This is done so that the predetermined value is not "overshot" thereby increasing the risk of skin damage. Additional controls are possible. For example, in another embodiment, the intensity may be scaled back when the parameter being monitored reaches 25%, 50% and 75% of the predetermined value.

According to another embodiment of the present invention, an apparatus and method for regulating the degree of skin permeabilization through a feedback system is provided. This apparatus and method may be similar to what has been described above, with the addition of further regulation of the degree of skin permeabilization. In this embodiment, however, the application of the skin permeabilizing device is terminated when desired values of parameters describing skin conductance are achieved. As the discussion proceeds with regard to FIG. 8, it should be noted that the descriptions above may be relevant to this description.

Figure 8:
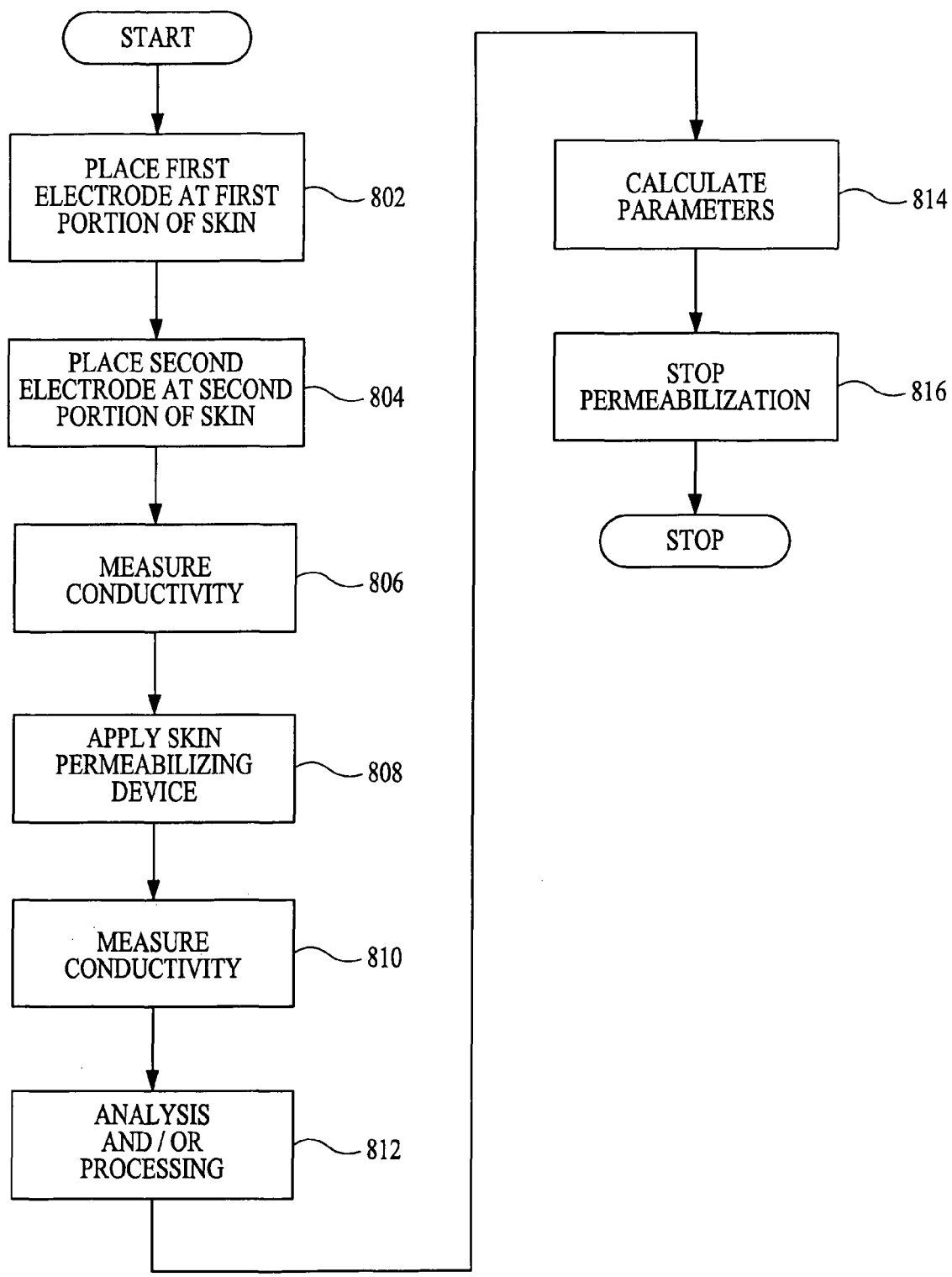
FIG. 8 depicts a flow chart of a method for controlled enhancement of transdermal delivery according to one embodiment of the present invention.

Referring to FIG. 8, a flowchart of the method is provided. In step 802, a first, or source, electrode is coupled in electrical contact with a first area of skin where permeabilization is required. As discussed above, the source electrode does not have to make direct contact with the skin. Rather, it may be electrically coupled to the skin through the medium that is being used to transmit ultrasound. In one embodiment, where an ultrasound-producing device is used as the skin permeabilizing device, the ultrasonic transducer and horn that will be used to apply the ultrasound doubles as the source electrode through which electrical parameters of the first area of skin may be measured and is coupled to the skin through a saline solution used as an ultrasound medium. In another embodiment, a separate electrode is affixed to the first area of skin and is used as the source electrode. In still another embodiment, the housing of the device used to apply ultrasound to the first area of skin is used as the source electrode. The source electrode can be made of any suitable conducting material including, for example, metals and conducting polymers.

Next, in step 804, a second, or counter, electrode is coupled in electrical contact with a second area of skin at another chosen location. This second area of skin can be adjacent to the first area of skin, or it can be distant from the first area of skin. The counter electrode can be made of any suitable conducting material including, for example, metals and conducting polymers.

In order to get an accurate electrical reading, the counter electrode should make sufficient contact with the skin. This can be achieved in a number of ways. In one embodiment, the counter electrode is applied directly to the epidermis of the skin. That is, the counter electrode is applied to an area of skin from which the stratum corneum has been removed. The stratum corneum may be removed in a number of ways. According to one embodiment, the stratum corneum is removed by tape stripping. In another embodiment, sufficient electrical contact between the skin and the counter electrode is created by using a counter electrode having a large surface area. More specifically, a conductive polymeric path or metallic foil patch having an area much larger than the skin area exposed to the skin permeabilizing device is used. The large area of the counter electrode in this embodiment decreases its impedances and allows accurate measurements of the electrical parameter of the area of skin exposed to the skin permeabilizing device. In one specific embodiment a conductive band is wrapped around the subject's arm and used as the counter electrode. In another embodiment, the counter electrode may be placed in a handle of the skin permeabilizing device, to which a subject grasps during operation.

In another embodiment, the counter electrode surrounds the skin permeabilizing device.

When the two electrodes are properly positioned, in step 806, an initial conductivity between the two electrodes is measured. This may be accomplished by applying an electrical signal to the patch of skin through the electrodes. In one embodiment, the electrical signal supplied may have sufficient intensity so that the electrical parameter of the skin can be measured, but have a suitably low intensity so that the electrical signal does not cause permanent damage to the skin, or any significant electrophoresis effect for the substance being delivered. In one embodiment, a 10 Hz AC source is used to create a voltage differential between the source electrode and the counter electrode. The voltage supplied should not exceed 500 mV, and preferably not exceed 100 mV, or there will be a risk of damaging the skin. In another embodiment, an AC current source is used. The current source may also be suitably limited. The initial conductivity measurement is made after the source has been applied using appropriate circuitry. In one embodiment a resistive sensor is used to measure the impedance of the patch of skin at 10 Hz. In another embodiment, a 1 kHz source is used. Sources of other frequencies are also possible.

In step 808, a skin permeabilizing device is applied to the skin at the first site. Any suitable device that increases the permeability of the skin may be used. In one embodiment, ultrasound is applied to the skin at the first site. According to one embodiment, ultrasound having a frequency of 20 kHz and an intensity of about 10 W/cm$^2$ is used to enhance the permeability of the patch of skin to be used for transdermal transport.

In step 810, the conductivity between the two sites is measured. The conductivity may be measured periodically, or it may be measured continuously. The monitoring measurements are made using the same electrode set up that was used to make the initial conductivity measurement.

Figure 9:
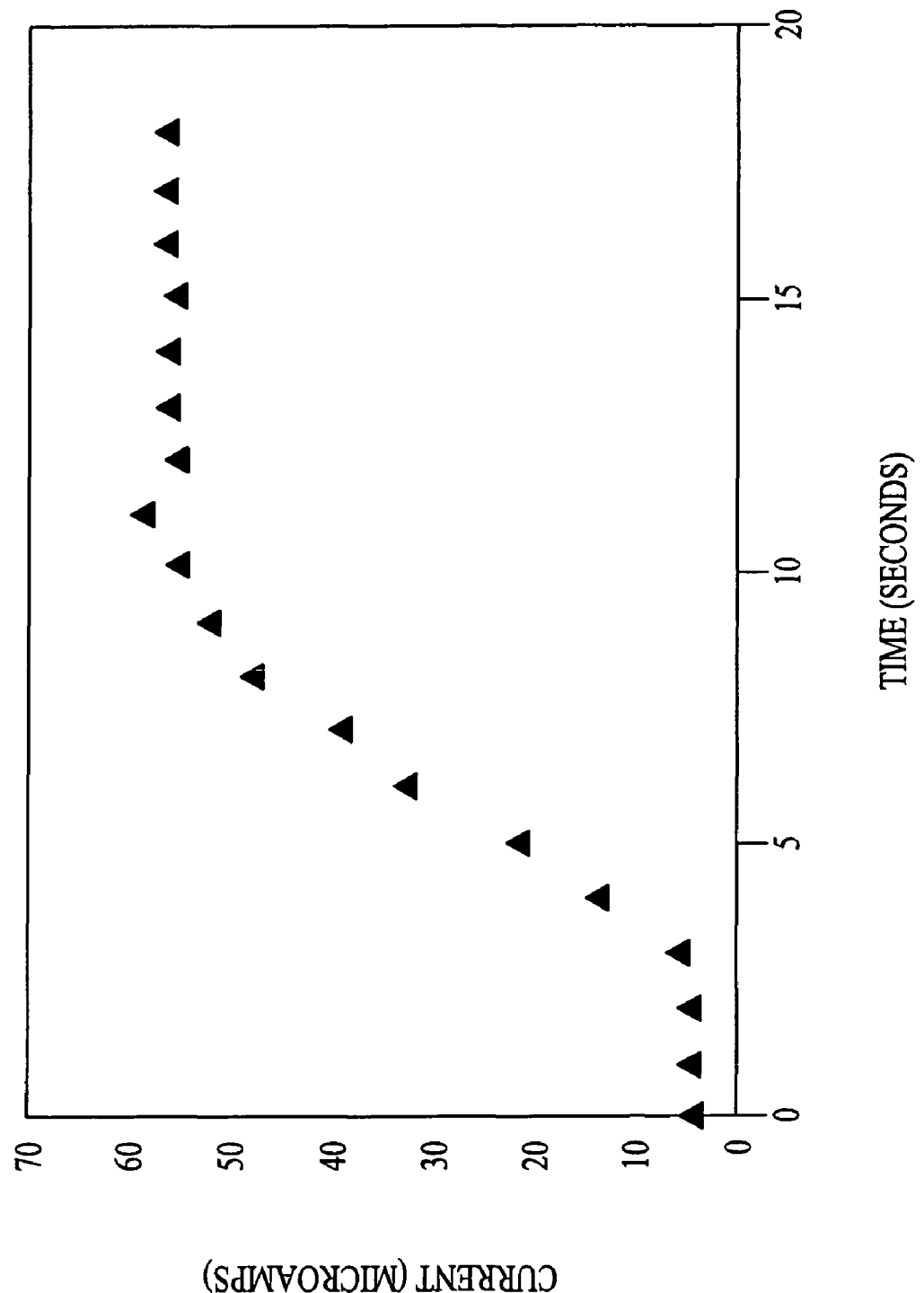
FIG. 9 depicts the time variation of the skin conductance while being exposed to ultrasound according to an example.

In step 812, mathematical analysis and/or signal processing may be performed on the time-variance of skin conductance data. Experiments were performed on human volunteers according to the procedure above, with ultrasound used as the method of permeabilization. Ultrasound was applied until the subjects reported pain. Skin conductivity was measured once every second during ultrasound exposure. After plotting the conductance data, the graph resembled a sigmoidal curve. The conductance data was in a general sigmoidal curve equation:

$$C = C_i + \frac{(C_f - C_i)}{1 + e^{S(t-t^*)}}$$

where:
C (is current;
$C_i$ is current at t=0;
$C_f$ is the final current;
S is a sensitivity constant;
$t^*$ is the exposure time required to achieve an inflection point; and
t is the time of exposure, FIG. 9 shows the time variation of the skin conductance while being exposed to ultrasound. The curve is a sigmoidal curve and can be fitted to the above equation. The line shown in FIG. 9 corresponds to a fit to the above equation. The values of fitted parameters were obtained and are plotted The value of t* corresponds to an exposure time required to achieve an inflection point (a point where the slope of the curve shown changes sign). The inflection time approximately indicates the time required to achieve half the total exposure.

Figure 10:
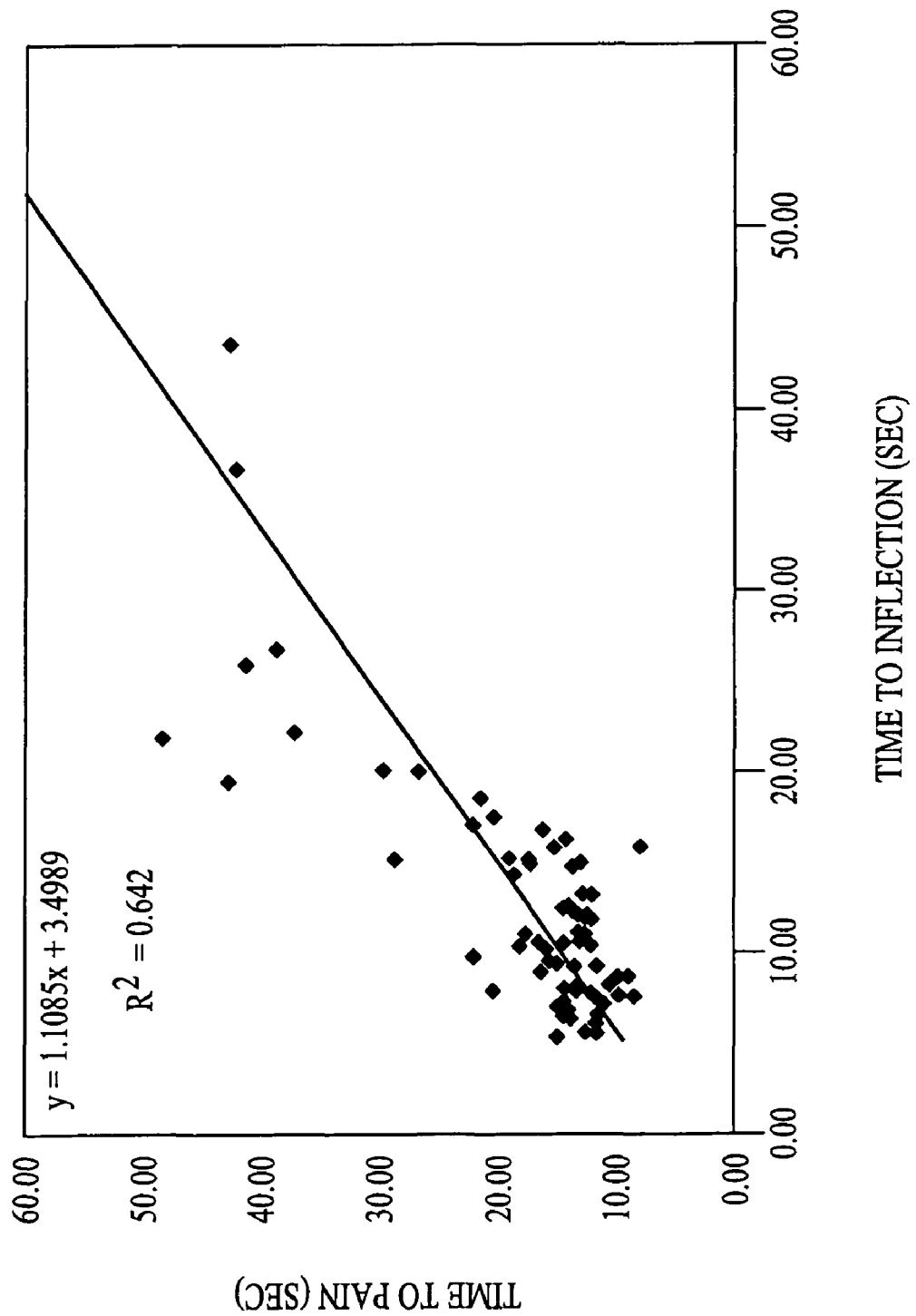
FIG. 10 shows a relationship between the inflection time and the time to pain on various volunteers according to an example.

FIG. 10 shows a relationship between the inflection time and the pain time on various volunteers. The data shows that the time to pain is proportional to the time to the inflection point on human volunteers. In this figure, R2 is the correlation coefficient, where a R2=1 indicates 100% correlation of the experimental data to the predicted values. Based on this data, a method can be developed to predict the required ultrasound exposure time.

Figure 11:
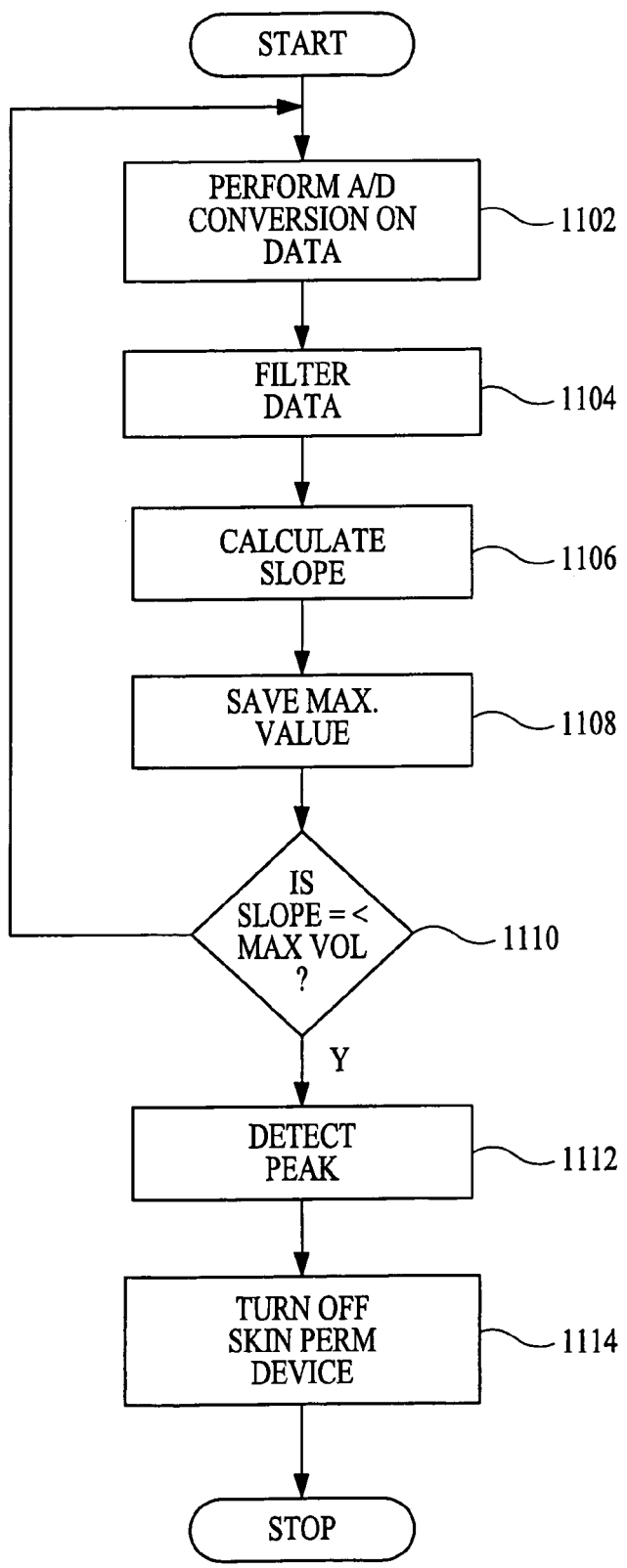
FIG. 11 depicts a flowchart of a method of determining when to terminate the application of ultrasound.
Figure 12A:
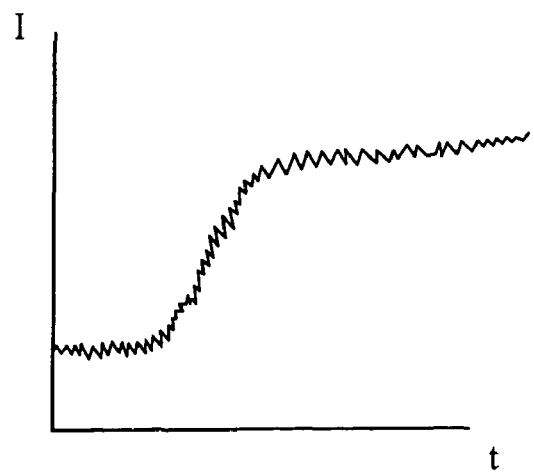
FIG. 12 depicts example graphs of the method of FIG. 11.
Figure 12B:
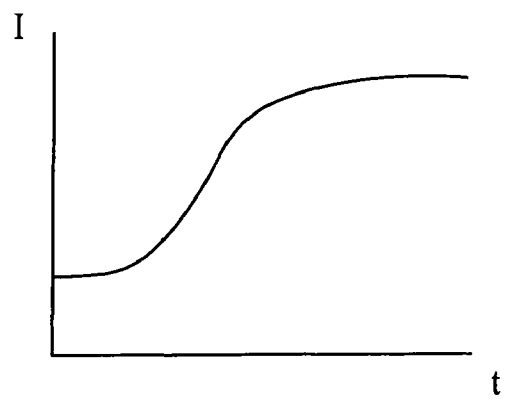
Figure 12C:
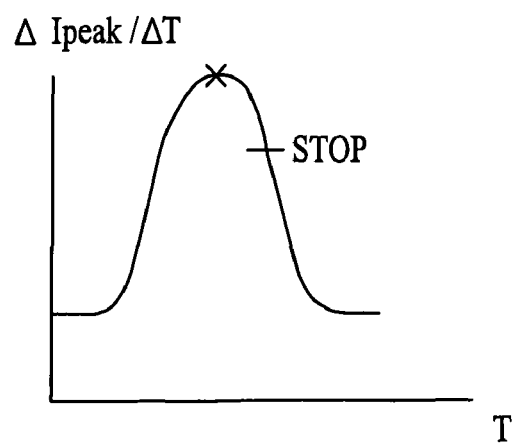

Referring to FIGS. 11 and 12, a flowchart depicting a method of determining when to terminate the application of ultrasound, and corresponding example graphs, are provided. In step 1102, A/D conversion is performed on the conductivity data. This results' in a graph similar to the one in FIG. 12a. Next, in step 104, filtering is performed on the digital data. As shown in FIG. 12b, the filtered data has a smoother curve than the unfiltered data of FIG. 12a. Next, in step 1106, the slope of the curve is calculated. In step 1108, the maximum value for the slope is saved. If the current value for the slope is greater than the maximum value that is saved, the maximum value is replaced with the current value. Next, in step 1110, if the slope is not less than or equal to the maximum value, the process returns to step 1102 to wait for a peak. If the slope is less than or equal to the maximum value, in step 1112 the process detects a peak, or point of inflection, shown in FIG. 12c, then, in step 114, terminates the application of ultrasound to the skin.

In one embodiment, the detection of the peak may be validated. This may be provided to ensure that the "peak" detected, in step 1112, was not noise, but was actually a peak.

In other embodiments, ultrasound may be applied even after the inflection point is reached. In one embodiment, ultrasound is applied for a predetermined time. This predetermined time may be based on a percentage of the time to reach the inflection point. For example, once the inflection point is reached, ultrasound continues to be applied for an additional 50% of the time it took to reach the inflection point. Thus, if it took 14 seconds to reach the inflection point, ultrasound is applied for an additional 7 seconds. Other percentages may be used, and this percentage may be based on factors including pain threshold and skin characteristics.

In another embodiment, ultrasound is applied until the slope decreases to a certain value. Referring again to FIG. 11, after the inflection point is reached, the slope decreases as ultrasound is applied. Thus, ultrasound may be applied until the slope decreases by a percentage, such as 50%, or to a predetermined value. As above, this determination is flexible and may vary from individual to individual.

In another embodiment, the current at the inflection point is measured, and then a percentage of this current is still applied. For example, if the inflection point is reached at 40 μamps, an additional 10% of this, for a total of 44 Lamps, may be reached. Again, this determination is flexible and may vary from person to person.

Referring again to FIG. 8, in step 814, the parameters describing the kinetics of skin conductance changes are calculated. These parameters include, inter alia, skin impedance, the variation of skin impedance with time final skin impedance, skin impedance at inflection time, final current, exposure time to achieve the inflection time, etc.

In step 816, the skin permeabilizing device applied in step 808 is terminated when desired values of the parameters describing skin conductance are achieved.

EXAMPLE

In vitro experiments were performed in accordance with a method according to one embodiment of the present invention. Pig skin was mounted on a diffusion cell and was exposed to ultrasound using 1% Sodium Lauryl Sulfate in water as a coupling medium. Skin conductance was measured by placing two electrodes across the skin. The impedances were measured at two frequencies: at 10 Hz, which is near the ultrasound range, and 1 kHz. The impedances measured at the frequencies differed by about 25 fold when the skin was impermeable. Upon sonication, the difference between the impedances at the two frequencies decreased. The differential impedance between the two frequencies decreased with time. When the skin was highly permeable, the impedances at two frequencies differed by only about 20%. SLS was removed from the chamber and the chamber was dried. A gel was placed in the chamber in contact with the skin. The gel was prepared by mixing glucose reagent from the Sigma™ kit 315 (10% by weight) into polyvinyl alcohol solution (20% by weight) in PBS. The gel was kept in the freezer to allow cross linking. The gel was clear in the beginning, and changed color to red when it came in contact with glucose.

2. Extraction and Analysis of at Least One Analyte in Body Fluid

Figure 13:
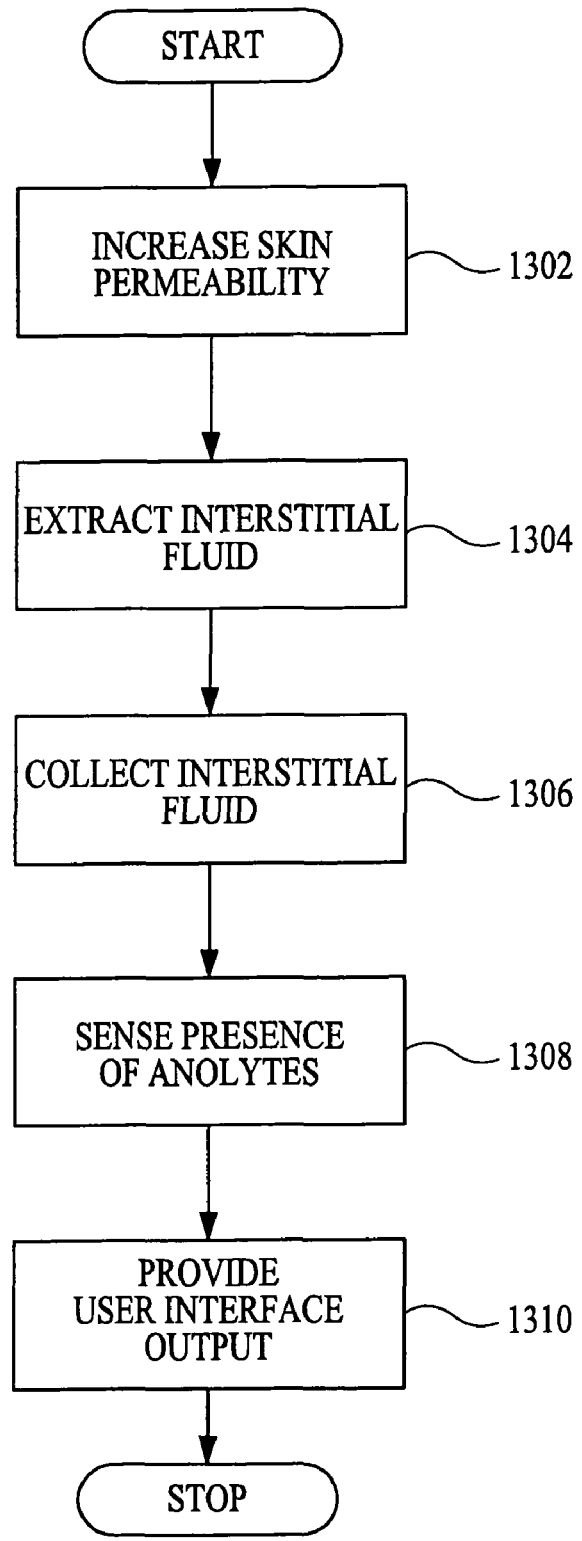
FIG. 13 depicts a flowchart of a method for extraction and analysis of at least one analyte in a body fluid according to one embodiment of the present invention.

According to another embodiment of the present, invention, ultrasound may be used to extract body fluids through or out of skin that has its permeability increased. Referring to FIG. 13, a flowchart depicting a method for extraction and analysis of at least one analyte in, a body fluid according to one embodiment of the present invention is disclosed. In step 1302, the permeability of the skin is increased. This may be accomplished by any suitable method for increasing the permeability of the skin, such as iontophoresis. In one embodiment, the permeability of the skin may be increased through the application of ultrasound.

As used herein, the term "interstitial fluid" include lymph, interstitial fluid, and serum that may be extracted from the body. It is also used to describe components of interstitial fluid.

In step 1304, interstitial fluid is extracted transdermally from the surface of the skin. Extraction can be performed after sonication or other permeation methods using a wide variety of different forces. These forces may include physical forces, chemical forces, biological forces, vacuum pressure, electrical, osmotic, diffusion, electro-magnetic, ultrasound, cavitation, mechanical, thermal, capillary forces, fluid circulation across the skin, electro-acoustic, magnetic, magneto-hydrodynamic, acoustic, convective dispersion, photo acoustic, by rinsing body fluid off skin, or by any combination of these forces.

Spatial and/or temporal positive and/or negative pressure modulation may be used. In spatial modulation, positive pressure is applied to an area of the skin, while a vacuum is applied to another area, assisting in the extraction of body fluid. In temporal modulation, vacuum and positive pressure alternate at about the same area of skin, assisting in the extraction of body fluid. The application of either spatial or temporal modulation may be continuous or discontinuous, and they may be applied separately or in combination.

In one embodiment, vacuum pressure may be applied to extract body fluid. Vacuum pressure may be applied continuously, or it may be applied discontinuously. When applied discontinuously, the vacuum may be applied in a pulsed fashion. A material that maintains the surface configuration of the skin (e.g., flat, convex, or concave), such as mesh, membrane, perforated metal, or other porous material, may be applied between the vacuum pressure and the skin while the vacuum pressure is applied. The vacuum can act through these structures and can be generated mechanically, electro-mechanically, chemically, or electrochemically. In another embodiment, the vacuum can be applied in such a manner so as to maintain the skin surface configuration with the vacuum alone.

In another embodiment, a chamber that is applied to skin can have a design (configuration and material properties) to localize high pressure gradient across skin and/or other tissues.

In another embodiment electrical forces may be applied. Electrical forces may be iontophoretic, electro-osmotic, or may be electroporation. A gel with an electric charge also may be applied, in order to encourage the absorption and evacuation of body fluid and components thereof.

In another embodiment, osmotic forces may be used. A gel or solution may be applied to the skin surface in order to encourage osmosis.

In another embodiment, ultrasound may be used to pump body fluid and fluid components, to levitate, to activate gas bodies, to produce cyclic impulse mechanical stress to the skin, to create microstreaming, to increase temperature, or to set up standing waves. Single or multiple sources of ultrasound may be used in combination with various characteristics of ultrasound, e.g., different frequencies, intensities, or coupling media, in order to encourage the extraction of body fluid.

In another embodiment, mechanical forces may used to extract body fluid. These forces may be achieved by, inter alia, a roller, a squeezer, a stretcher, iris compressor/tensioner device, etc. to increase the volume of the body fluid that is extracted.

Figure 14:
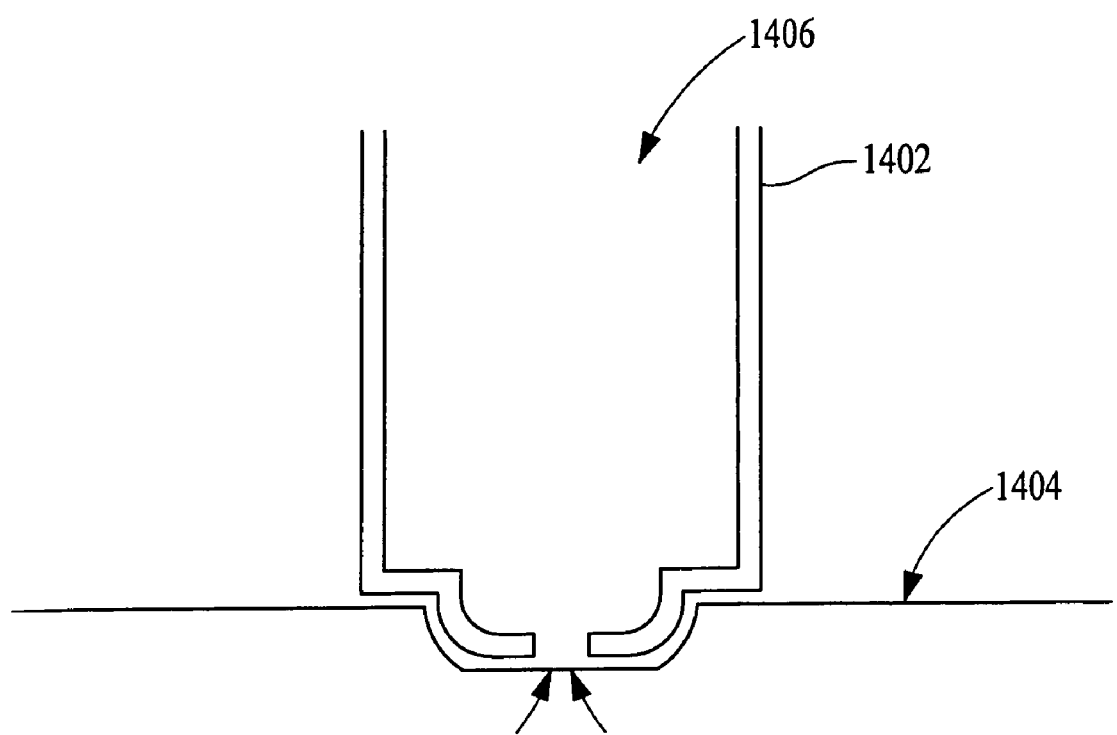
FIG. 14 depicts a drawing of a tensioner according to one embodiment of the present invention.

In one embodiment, a tensioner is used to extract body fluid. Referring to FIG. 14, which depicts an embodiment of a tensioner, tensioner 1402 consists of a convex geometry held against the skin 1404. By pressing tensioner 1402 against skin 1404, body fluid may be collected within cavity 1406 of tensioner 1402.

In another embodiment, thermal forces may be used to extract body fluid. The skin temperature may be increased using electricity, chemical, ultrasonic, or optical energy sources or methods and/or utilize temperature sensitive polymers to swell or contract a gel, membrane, and/or solid to encourage the absorption and evacuation of body fluid and components thereof. Temperature sensitive polymers may be used to move a piston or membrane to push or suck fluid. Examples of such polymers include, inter alia, poloxymers.

In another embodiment, chemical forces are used Chemical substances may be used to augment convective and/or diffusive forces as a means to extract additional body fluid, and/or to enhance transport and/or accumulation of body fluids at specific body sites. A hydrogel with an incorporated trapped, or immobilized bioactive molecules such as enzyme would allow for extraction by osmosis into a sensing scaffold.

In another embodiment, pH/ionic forces may be used These forces may be used to change the material properties and characteristics, e.g., hydrophilic material to a hydrophobic material. A pH/ionic sensitive membrane and/or gel may be swollen and contracted in order to encourage the absorption and evacuation of body fluid and components thereof.

In another embodiment, capillary forces may be used. These forces may be used to assist in fluid transport across skin pores.

Referring again to FIG. 13, in step 1306, the body fluid and components thereof are collected. This collection may be accomplished by absorption, adsorption, phase separation, mechanical forces, electrical forces, chemically induced forces, or a combination thereof. Preferably, a humid environment is created and maintained in order to control evaporation of analytes during extraction. The collected volume of body fluid may be the same as the volume extracted, or it may be a fixed constant volume.

In one embodiment, absorption or adsorption may be used. In this embodiment, the body fluid may be collected into a gel, which contains a captive enzyme. A polymeric, metallic, or ceramic screen, scaffold, mesh, or membrane, or a combination may be used to do this. These materials may also be a component of a sensor.

In one embodiment, phase separation may be used. Body fluid may be isolated by combining the fluid with an appropriate density immiscible fluid. The body fluid may be collected into a conical chamber.

Another use of phase separation is achieved by first applying a hydrophobic coating on the skin prior to the extraction step. After the extraction, body fluid is present in the form of droplets on the hydrophobic coating.

In another embodiment, mechanical forces may be used to collect body fluids. This includes forces such as vacuum, pressure, and acoustic forces. Dispersed body fluid may be collected over a greater area to a smaller area using a microfluidic channel against the skin. A means to evacuate the fluidic path may include the introduction of a liquid and/or gas. This means to evacuate may be applied to all collection processes, and not just mechanical collection.

In another embodiment, electrical collection may be used. In this embodiment, solid, liquid droplets, or gas are charged and transported (moved) from skin to a sensor or to a collecting compartment using electrical forces.

In another embodiment, chemical collection may be used. A hydrophilic gel may be used to collect body fluids. The material properties and characteristics may be changed, e.g., hydrophilic material to a hydrophobic material, in order to encourage the absorption and evacuation of body fluid and components thereof.

In another embodiment, capillary collection may be used. Body fluid may be collected into a capillary or capillaries. This allows for quantitative volume or a method to move fluid to a sensor. The capillary or capillaries may be filled with multiple fibers to increase the surface area on which a liquid's adhesive forces can act. This method may be used in conjunction with a chemical substance and/or other driving forces.

In step 1308, the concentration of analytes in body fluid is sensed. Sensing the concentration of an analyte present in body fluid may be accomplished by employing electrochemical, optical, acoustical, biological, and enzymatic technology in combination or alone. A sensor or sensors can be disposable, replenishable, discrete, or continuous.

According to one embodiment, a sensing device may have a sensor or sensors capable of detecting more than one analyte. If one or more, or a combination of several analytes exists in stable and/or predictable physiologic, concentrations, the ratio of one analyte to the other would allow for concentration detection and self-calibration. Neither the volume of the body fluid or the dilute volume needs be known.

A sensing device presented with a known volume of body fluid (undiluted) and a known volume of diluent would not require frequent calibration.

In one embodiment, body fluid is extracted and optical analysis is performed on the body fluid.

In another embodiment, the body fluid is extracted and electrochemical analysis is performed on the body fluid.

In another embodiment, the body fluid is extracted and the acoustical emission of an analyte undergoing a chemical reaction is detected and analyzed.

In another embodiment, the body fluid is extracted, and living cells may be used to sense a concentration of an analyte in body fluid.

In another embodiment, the body fluid is extracted, and thermal analysis is performed on the body fluid.

In step 1310, information is provided for the user interface. A user interface may provide features for both daytime and nighttime monitoring. In one embodiment, this may include alarms for high/low analyte concentrations, may provide access to trends and history, and may enable a prediction of future concentration values. The user interface may provide the ability to download history. Other convenience features, such as a low battery indicator, may be included in the user interface. The battery may be solar, nickel cadmium, standard alkaline, or lithium ion.

In another embodiment, after the permeability of the skin is increased, the presence of the analyte may be sensed without extraction. Infrared light, for example, may be used to sense the presence of an analyte, with less interference from $H_2O$.

In another embodiment, after the permeability of the skin is increased, at least one analyte is permitted to passively diffuse through the skin. The analyte may be collected in a gel used as a collecting device, and a sensing device, attached to the gel, may be used to sense the presence of the analyte.

In another embodiment, additional methods for generating cavitation and convectional flow may be applied with, before, after, or instead of the ultrasound application for skin permeabilization and/or extraction and/or collection steps. These methods include the use of a propeller, fly wheel, transverse needle, and local shear induced permeabilization.

Figure 15:
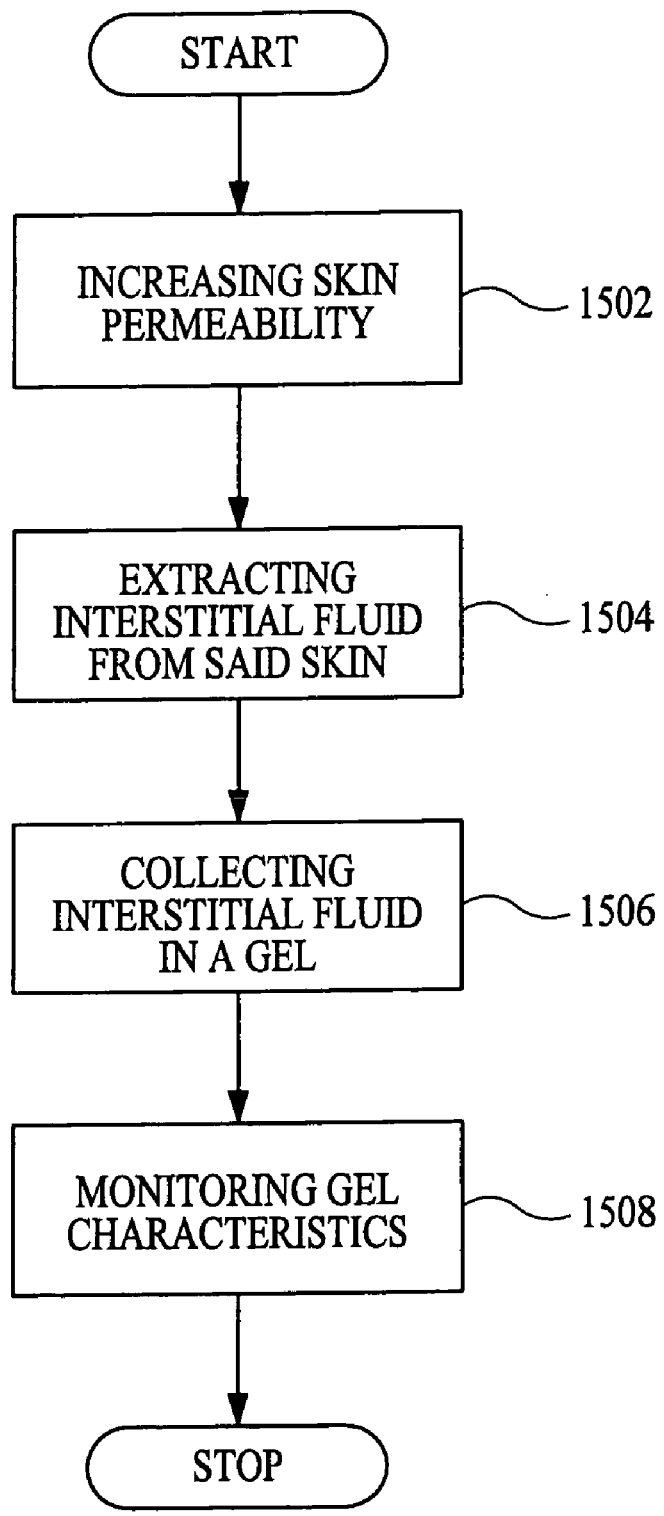
FIG. 15 depicts a flowchart of a method of determination of blood glucose according to one embodiment of the present invention.

In another embodiment the non-invasive method disclosed herein may be used to determine the level of blood glucose. Referring to FIG. 15, in step 1502, the permeability of the skin is increased. This may be achieved by any suitable method. Preferably, ultrasound is applied as discussed above.

In step 1504, the interstitial fluid is extracted from the skin. This may be accomplished by any suitable method, including those discussed above. Preferably, a vacuum is applied to extract the interstitial fluid from the skin.

In step 1506, the interstitial fluid is collected. This may be accomplished by any suitable method, including those discussed above. Preferably, the interstitial fluid is collected into a gel containing glucose sensitive reagents. The gel may change color when it comes in contact with glucose.

In step 1508, the color change of the gel is monitored to determine the glucose concentration in the interstitial fluid.

In another embodiment, ultrasound may be used for detection (evaluation, follow up treatments) of skin and/or other subcutaneous abnormalities presented by pathological concentrations of specific analytes, or detection of specific components administered to the site and detection of their elimination or conversion (psoriasis, skin malignancies, etc.). This approach may be used, for example, in extracting analytes or reagents from skin-affected sites (lesion plaques), tumors, etc.

In another embodiment, the delivery and/or removal of endogenous and non-endogenous components from the skin by the application by a Force is disclosed. Forces, such as ultrasound, electrical, magnetic, capillary, mechanical, chemical, electromagnetic, osmotic, concentration gradient, or combinations thereof may be used in applications such as, inter alia, removal of residual surfactant, cavitation enhancers, tattoo bleach, and botox (remove from forehead, and neck lines, reduce sweating).

In another embodiment, sensing components may be delivered into the skin to analyze interstitial fluid components in situ. The sensing components may also be delivered into the skin to measure emitted products or reagents of any sensing reaction (chemical or enzymatic).

3. Sonophoretic Drug Delivery

A drug is defined as a therapeutic, prophylactic, or diagnostic molecule or agent, that may be in a form dissolved or suspended in a liquid, solid, or encapsulated and/or distributed in or within micro or nanoparticles, emulsion, liposomes, or lipid vesicles. Drug delivery is defined as the delivery of a drug into blood, lymph, interstitial fluid, cells, tissues, and/or organs, or any combination thereof.

Figure 16:
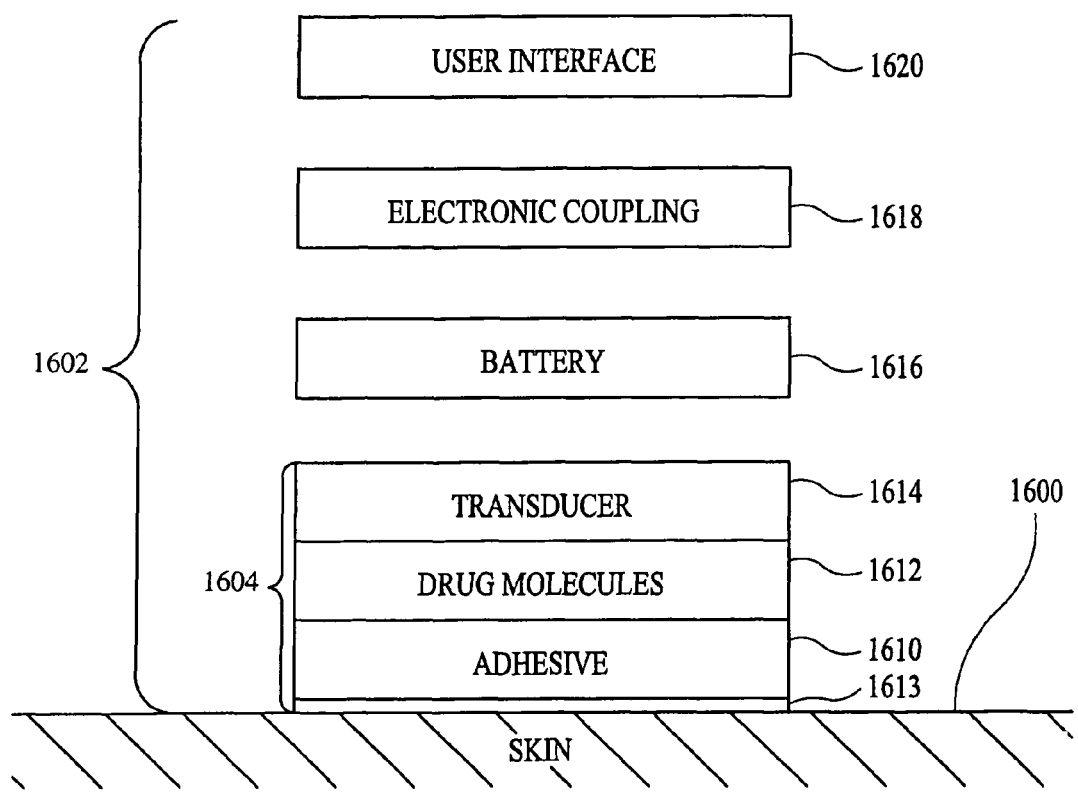
FIG. 16 illustrates a drug delivery patch apparatus in accordance with one embodiment of the present invention.

Referring to FIG. 16, an active patch drug delivery apparatus 1602 that is attached to skin 1600 is depicted. Drug delivery apparatus 1602 includes patch 1604. Patch 1604 includes adhesive 1610, drug molecules 1612 and transducer 1614. Patch 1604 is an active patch. Adhesive 1610 acts as an attaching device. Alternatively, the attaching device may be a vacuum, band, or strap. As transducer 1614 oscillates, the permeability of skin 1600 is increased in accordance with the present invention and drug molecules 1612 are delivered to and/or through skin 1600, or/and after skin 1600 is permeabilized, drug molecules 1612 are transported through skin 1600 to the capillaries and blood vessels below skin 1600. A limiting step membrane 1613 may be located between skin 1600 and drug molecules 1612.

Transducer 1614 preferably operates at a frequency in the range of between 20 kHz to 2.5 MHz, using appropriate electrical signal generators and amplifiers. Transducer 1614, more preferably, is operating at a frequency in the range of between 20 and 200 kHz. Other ultrasound parameters include, but are not limited to, amplitude, duty cycle, distance from the skin, coupling agent composition, and application time and may be varied to achieve sufficient enhancement of transdermal transport. The intensity preferably varies from 0 to 20 $W/cm^2$. Further, transducer 1614 may be configured as a cylinder, a hollow cylinder, a hemispherical configuration, conical configuration, planer configuration or rectangle configuration. Transducer 1614 may also consist of an array of acoustic elements that are swept in time. Transducer 1614 may be comprised of quartz, PVDF, ceramic including PZT and screen printed ceramic, magnetostrictive, or composite material including molded ceramic and benders. Transducer 1614 may be used alone or in conjunction with other forces, or contributors, to enhance drug delivery. These other forces, or contributors, include, but are not limited to, a magnetic field including electromagnetic forces, an electrical current or iontophoresis, mechanical skin manipulation, chemical enhancement, heat, and osmotic forces.

Transducer 1614 administers ultrasound preferably at frequencies of less than or equal to about 2.5 MHz, preferably at a frequency that is less than 1 MHz, and more typically in the range of about 20 to 100 kHz. Exposures to ultrasounds from transducer 1614 are typically between about 5 seconds and about 10 minutes continuously, but may be shorter and/or pulsed, for example, at 100 to 500 msec pulses every seconds for a time sufficient to permeabilize the skin. The ultrasound intensity is of a level that preferably does not raise skin 1600's temperature more than about 1 to 2 degrees Centigrade and does not cause permanent damage to the skin. The intensity typically is less than 20: $W/cm^2$, preferably less than 10 $W/cm^2$. Intensity in time of application is inversely proportional to exposure time, so that high intensities are applied for shorter period of times in order to avoid skin damage. It should be noted that although normal low range ultrasound is 20 kHz, comparable results are achieved by varying the frequency to less than 20 kHz, or into the sound region.

The time needed for permeabilization is: dependant upon the frequency and intensity of the ultrasound from transducer 1614 and the condition of skin 1600. At 20 kHz, for example, an intensity of 10 $W/cm^2$, with a duty cycle of 50 percent, skin 1600 is permeabilized sufficiently in about 5 minutes if skin 1600 is on a human forearm.

Permeabilizing ultrasound may be applied for a predetermined amount of time or may be applied only until permeabilization is attained. Because skin 1600 characteristics or properties may change over time, based on aging, diet, stress, and other factors, it may be preferable to measure permeability as ultrasound is applied to minimize the risk of skin 1600 damage. Several methods may be used to determine when sufficient permeabilization has been reached. One method measures relative skin conductivity at the permeabilization site versus a reference point. These measurements are performed by applying a small AC or DC electric potential across two electrically isolated electrodes in contact with skin 1600. Electric current flowing through these electrodes is measured using an ammeter and skin 1600 resistance is measured using the values of the potential and current. Drug delivery patch apparatus 1602 may serve as one of the electrically isolated electrodes in contact with skin 1600. Preferably, drug delivery patch apparatus 1602 permeabilizes skin 1600 prior to the conductivity tests.

Another way to determine when sufficient permeabilization has been reached is to measure conductivity. Fully permeabilized skin has a resistance of no more than about 5 k$\Omega$ measured across approximately 1.7 $cm^2$. Another method is to detect and/or quantitate the transdermal movement of an analyte, such as creatinine, calcium or total ions, that is present in interstitial fluid in a fairly constant amount, and may be used either to calibrate the concentration of analyte to be extracted and quantified, or as a measure of permeabilization. The higher the constant analyte flux, the greater degree of permeabilization. The degree of permeability also may be monitored using a sensor attached to drug delivery patch apparatus 1602 that determines the concentration of drug molecules 1612 being delivered or an analyte being extracted. As the permeability increases, the drug concentration within drug delivery patch 1602 decreases.

Drug delivery patch apparatus 1602 also may be applied to pretreated skin 1600. In other words, permeabilization of skin 1600 is already achieved. Drug delivery patch apparatus 1602 is placed over pretreated skin 1600 to deliver drug molecules 1612. Any known device may be used to pre-treat skin 1600, including, but not limited to, physical forces, chemical forces, biological forces, vacuum pressure, electrical forces, osmotic forces, diffusion forces, electromagnetic forces, ultrasound forces, cavitation forces, mechanical forces, thermal forces, capillary forces, fluid circulation across the skin, electro-acoustic forces, magnetic forces, magneto-hydrodynamic forces, acoustic forces, convective dispersion, photo-acoustic forces, by rinsing body fluid off skin, and any combination thereof.

Drug molecules 1612 include a variety of bio-active agents, including protein and peptides. Other materials include nucleic acid molecules such as vaccines including therapeutic proteins synthetic organic and inorganic molecules including anti-inflammatories, anti-virals, anti-fungal, anti-biotics, and local anesthetics, and saccharides and polysaccharides. Drug molecules 1612 may be administered in an appropriated pharmaceutically acceptable carrier having an absorption coefficient, similar to water, such as an aqueous gels, ointment, lotion, or suspension. Drug molecules 1612 also may be contained with adhesive 1610 that attaches to skin 1600. Further, drug molecules 1612 also may be encapsulated or suspended in a liquid, gel, or solid matrix within patch 1604.

Drug delivery patch apparatus 1602 also includes a battery 1616. Battery 1616 acts as a power source for transducer 1614. Battery 1616 provides a relatively high energy burst. Drug delivery patch apparatus 1602 also includes electronic coupling 1618 that serves as the drive electronics for drug delivery patch apparatus 1602. Drug delivery patch apparatus 1602 also includes user interface 1620.

In one embodiment, patch 1604 includes transducer 1614, drug molecules 1610, and adhesive 1610. In another embodiment, patch 1604 includes transducer 1614, drug molecules 1612, adhesive 1610, battery 1616, electronic coupling 1618, and user interface 1620. In another embodiment, patch 1604 includes transducer 1614, drug molecules 1612, adhesive 1610, and battery 1616. In another embodiment, adhesive 1610 is to the side of transducer 1614 and drug molecules 1612.

Battery 1616, electronic coupling 1618, and user interface 1620, may be located elsewhere on a user and in communication with patch 1604 via hard wire or telemetry. In another embodiment, user interface 1620 may be located elsewhere on the user and is in communication with patch 1604 via hard wire, telemetry, infra-red, or fiber optic means. Thus, the elements of drug delivery apparatus 1602 may be detachable and portable from each other. Further, any of the components of drug delivery apparatus 1602 may be disposable or reusable. For example, patch 1604, which includes transducer 1614, drug molecules 1612 and adhesive 1610 may be disposed after detachment from skin 1600. However, battery 1616, electronic coupling 1618, and user interface 1620 may be re-usable with further patches 1604.

In one embodiment, transducer 1614 operates alone to push drug molecules 1612 through and to skin 1600. Alternatively, drug delivery patch apparatus 1602 and transducer 1614 may operate in conjunction with a driving force that further facilitates the transdermal transport of drug molecules 1612. These forces include, but are not limited to physical forces, chemical forces, biological forces, vacuum pressure, electrical forces, osmotic forces, diffusion forces, electromagnetic forces, ultrasound forces, cavitation forces, mechanical forces, thermal forces, capillary forces, fluid circulation across the skin, electro-acoustic forces, magnetic forces, magneto-hydrodynamic forces, acoustic forces, convective dispersion, photo-acoustic forces, by rinsing body fluid off skin, and any combination thereof.

Figure 17:
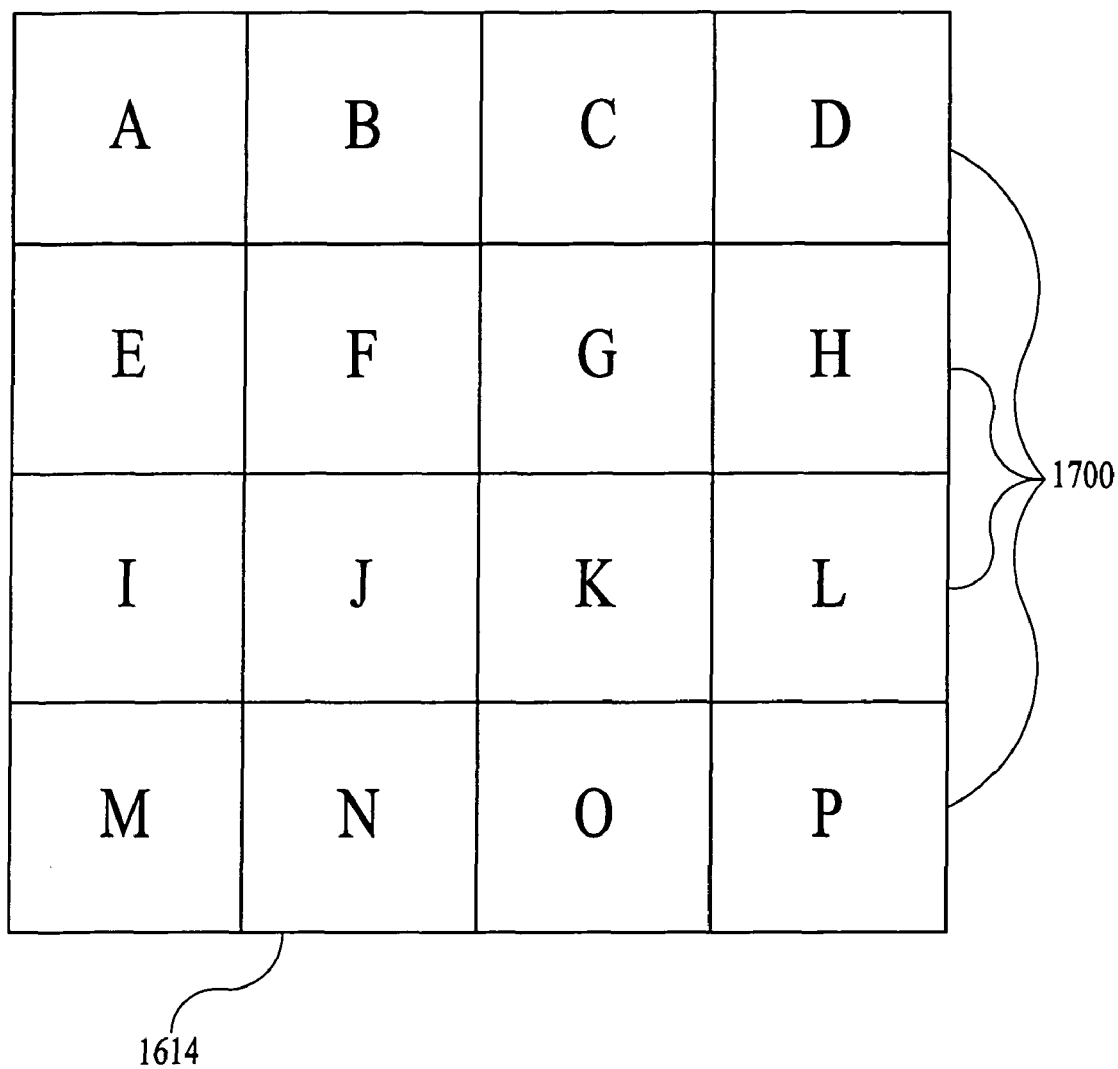
FIG. 17 illustrates a cross-sectional, view of a transducer in accordance with one embodiment of the present invention.

Referring to FIG. 17, an embodiment of transducer 1614 is depicted. Transducer 1614 may be an array of acoustic elements that are swept in time as ultrasound is applied to drug molecules 1612, and through adhesive 1610 to skin 1600. Acoustic elements 1700 comprise transducer 1614. Elements 1700 are depicted as squares within a larger square. Elements 1700 are not limited to this configuration and may be configured as a cylinder, a hollow cylinder, hemispherical, conical, planer, rectangular. Each acoustic element of elements of 1700 may be swept individually or within a group as transducer 1614 is activated. For example, element A activates, followed by elements B and E, then followed by elements C, F, and I, and so on. Element P may be activated last as transducer 1614 is swept. Further, acoustic elements 1700 may comprise fingers. Referring to FIG. 17, a finger may be depicted as elements A, E, I, and M. Each finger may be activated or swept in time. Acoustic elements 1700 may be configured to channel the ultrasound energy from transducer 1614 to a specified area in 100 smaller than the area of transducer 1614.

Figure 18:
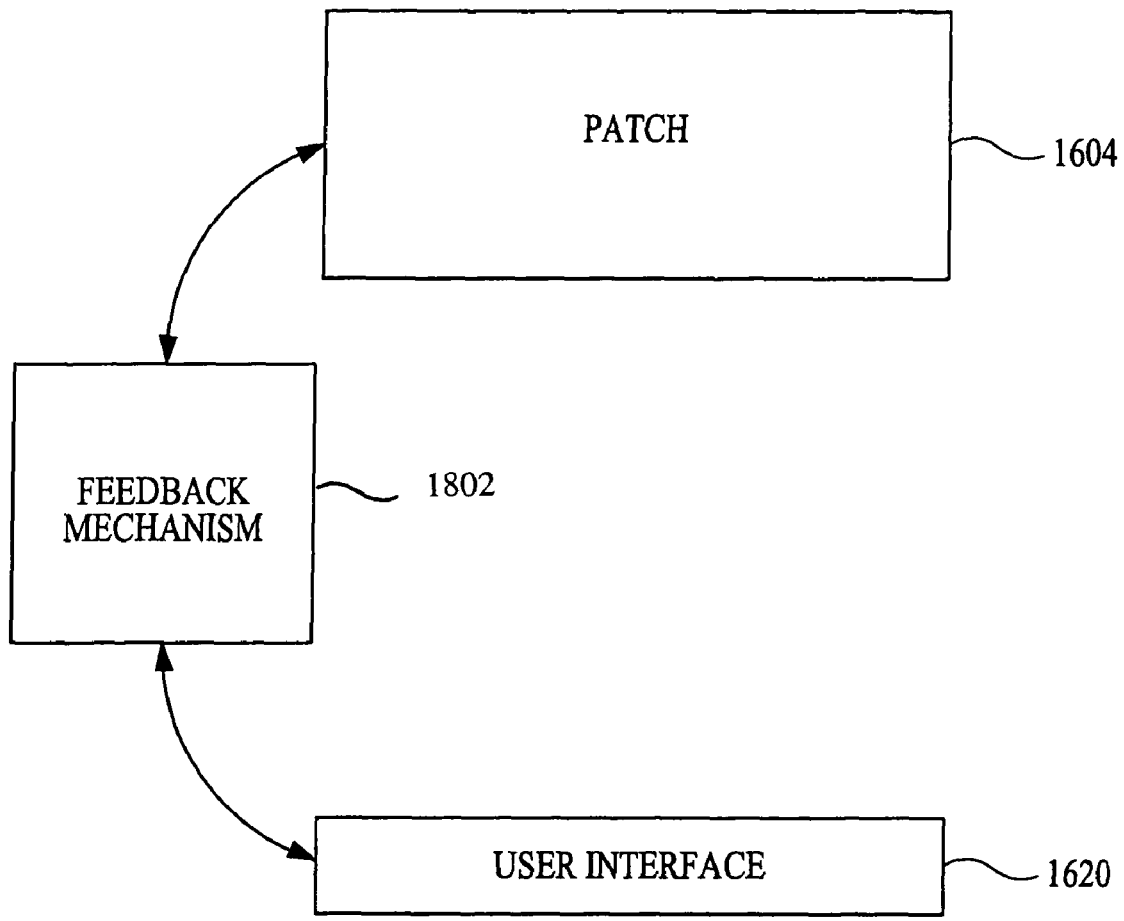
FIG. 18 illustrates a drug delivery patch apparatus having a feedback mechanism in accordance with one embodiment of the present invention.

Referring to FIG. 18, patch 1604 and user interface 1620 are coupled to feedback mechanism 1802. Feedback mechanism 1802 may be detachable from user interface 1620. Alternatively, feedback mechanism 1802 may be contained within user interface 1620. Thus, feedback mechanism 1802 may be contained within drug delivery patch apparatus 1602. Feedback mechanism 1802 provides for programming of drug delivery rates or pre-set doses of drug molecules 1612. Feedback mechanism 1802 also may provide memory to record or display historical delivery data to user interface 1620. Feedback mechanism 1802 communicates the on time of transducer 1614 to user interface 1620 for display to the user. Feedback mechanism 1802 also may provide alarms for low drug molecules 1612 and/or low power in battery 1616. Thus, feedback mechanism 1802 alerts a user via a user interface 1620 that drug molecules 1612 and patch 1604 needs to be replenished or that drug delivery patch apparatus 11602 is low on power.

Feedback mechanism 1802 also may monitor the amount of drug molecules 1612 delivered via transdermal transport. Feedback mechanism 1802 also may monitor the amount of ultrasonic energy, or other driving forces listed above, applied to skin 1600 by transducer 1614. Limits may be set in feedback mechanism 1802 to limit the ultrasound energy from transducer 1614 so as to no irritate or damage skin 1600. Feedback mechanism 1802 also may monitor the concentration of drug molecules 1612 remaining in patch 1604. Feedback mechanism 1802 also may monitor the concentration of drug molecules or analytes in the interstitial fluid, blood, and other body fluids. Feedback mechanism 1802 also, may monitor the amount of cavitation produced by the application of ultrasound energy. Feedback mechanism 1802 also may monitor the degree of physiological effects such as blood pressure, EMG, EEG, and ECT feedback in order to measure delivery of drug molecules 1612. Feedback mechanism 1820 also may provide connections with additional patches or testing devices in order to perform conductivity tests.

4. Transdermal Vaccination by Sonophoresis

Generally, vaccines are administered for the prevention, amelioration or treatment of infectious diseases. Vaccines are commonly used to provide immunity from diseases such as influenza, poliomyelitis, varicella zoster (chicken pox), measles, as well as several other diseases.

A vaccine is generally made from an antigen isolated or produced from the disease-causing microorganism. An antigen is defined as "anything that can be bound by an antibody." This can be an enormous range of substances from simple chemicals, sugars, small peptides to complex protein complexes., such as viruses. The small antigens are not, however, immunogenic in themselves, and need to be coupled to a carrier to elicit an immune response.

Typically, the vaccine is delivered to the bloodstream by an invasive method, such as an injection. The B cells in the blood stream respond to the antigen by producing antibodies. These antibodies bind to the antigen to "neutralize," or inactivate it. Memory cells are also produced, and remain ready to mount a quick protective immune response against subsequent infection by the same disease-causing agent.

Immunization is the process of causing immunity by injecting antibodies or provoking the body to make its own antibodies against a certain microorganism. Immunization may be a result of a vaccination.

As discussed above, the use of ultrasound to facilitate transdermal transport is known. The mechanism by which ultrasound is used to facilitate transdermal transport has differed. In the context of transdermal delivery systems, ultrasound was initially a driving force that essentially pushed drugs through the skin and into the circulatory system. Ultrasound also increases the permeability of the skin. In other words, application of ultrasound having a particular frequency disorganizes the lipid bi-layer in the skin, thereby increasing the permeability of the skin. In this context, drugs may be delivered to the body through the skin, or an analyte may be extracted from the body through the skin. System and methods for the application of ultrasound to enhance the permeability of skin, as well as the extraction of body fluids are discussed, above.

Although the permeability of the skin is increased by the application of ultrasound, a driving force is still required for transdermal transport, but the required intensity of the driving force is decreased. For example, a concentration gradient is generally a sufficient driving force for transdermal transport through skin whose permeability has been enhanced using ultrasound. The permeability enhancement that results from the application of ultrasound is due at least in part, to cavitation that is caused by the ultrasound.

Figure 19:
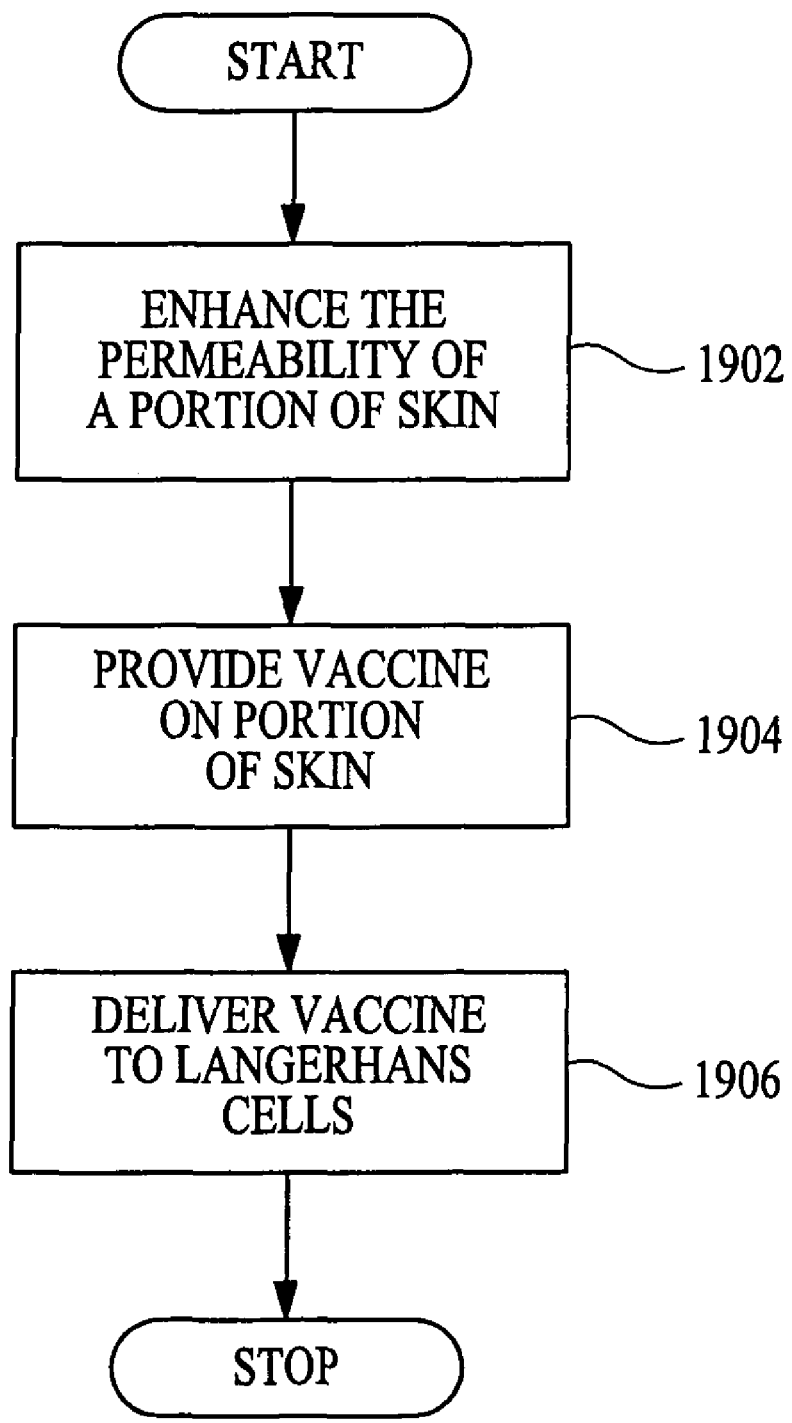
FIG. 19 depicts a flowchart of the method for transdermal vaccination by sonophoresis according to one embodiment of the present invention.

FIG. 19 depicts a method for transdermal vaccination by sonophoresis according to one embodiment of the present invention. Referring to FIG. 19, in step 1902, the permeability of the skin is increased. This may be achieved by several methods, including those discussed above.

In one embodiment, ultrasound may be applied at about 10 $W/cm^2$, with a duty cycle of about 50%. Ultrasound may be applied at a distance from the skin of about 0.5 mm to 1 cm, and for an application time off from about 30 seconds to about 5 minutes.

A coupling medium may be used between the transducer and the skin, and may contain aqueous or non-aqueous chemicals including, but not limited to, water, saline, alcohol, including ethanol and isopropanol (1-100% mixtures with saline), surfactants, fatty acids such as linoleic acid (0.1-2% mixtures in ethanol-water (50:50) mixture), azone (0.1-10% mixtures in ethanol-water (50:50) mixture), 01-50% polyethylene glycol in saline, 1-100 mM EDTA, EGTA, or 1% SLS and silica particles. The coupling media provide effective transfer of ultrasound energy from transducer to the skin. Appropriate mixtures of these coupling media may also enhance cavitation activity inside, on the surface, or near the skin, thus inducing more effective transport of molecules across the skin.

In step 1904, after the permeability of the skin is increased, sonication is terminated, and a vaccine is provided on the permeated skin. In one embodiment, the vaccine may be incorporated into a transdermal patch. Other forms of the vaccine, such as gels and liquids, may also be used.

The vaccine may comprise as the active ingredient a peptide, protein, allergen, or other antigen, or DNA encoding any of the foregoing and may also include other adjuvants normally employed. These vaccines may be used as cancer vaccines, tetanus vaccines, etc.

In step 1906, the vaccine is delivered to the skin cells. In one embodiment, the vaccine is delivered to skin cells, including Langerhans cells, dendritic cells, and keratinocytes.

In one embodiment, the vaccine is delivered to the Langerhans cells. The Langerhans cells are the cells responsible for capturing a vaccine and presenting it to the Lymphatic system, and eliciting an immune response. The vaccine may be delivered to other cells to illicit an immune response.

In one embodiment, the vaccine may diffuse to the skin cells, including Langerhans cells, dendric cells, and keratinocytes. Once the vaccine is received by the skin cells, the vaccine is transported to the lymph nodes efficiently, increasing the efficiency of vaccination.

In another embodiment, the vaccine is transported transdermally through, in, or into the skin and into the bloodstream, wherein it acts as if it were injected in a conventional manner.

In another embodiment of the present invention, the vaccine is provided simultaneously with the application of ultrasound. The ultrasound in this embodiment is used both to permeabilize the skin, as well as and to deliver the vaccine transdermally to the Langerhans cells. The ultrasound acts as a driving force. Examples of using ultrasound to transport drugs from a patch are discussed above.

In another embodiment of the present invention, ultrasound is applied to the skin to increase the permeability of the skin. Once the vaccine is provided, additional driving forces are provided to deliver the vaccine to the body. Examples of driving forces include, inter alia, physical forces, chemical forces, biological forces, vacuum, electrical forces, osmotic forces, diffusion forces, electro-magnetic forces, ultrasound forces, cavitation forces, mechanical forces, thermal forces, capillary forces, fluid circulation across the skin, electro-acoustic forces, magnetic forces, magneto-hydrodynamic forces, acoustic forces, convective dispersion, photo acoustic forces, and any combination thereof.

In another embodiment, ultrasound can be used to induce irritation and inflammation of the skin. Inducing irritation and inflammation may make the vaccine placed on the skin more effective in inducing an immune response.

In another embodiment, chemical enhancers may be used to increase the permeability of the skin.

Although the present invention has been described in detail, it should be understood that various changes, substitutions, and alterations can be made without departing from the intended scope as defined by the appended claims.

What is claimed is:

1. A method for enhancing a permeability of an area of skin for drug delivery or analyte extraction comprising:
   increasing the permeability of the area of skin with a skin permeabilizing device, wherein the skin permeabilizing device comprises a permeability monitoring circuit for monitoring at least one electrical parameter of the area of skin indicative of skin permeability and wherein the skin permeabilizing device permeabilizes the skin using mechanical force;
   applying electricity in the form of an alternating current to the area of skin;
   monitoring the at least one electrical parameter of the area of skin using the permeability monitoring circuit of the skin permeabilizing device; and
   controlling the mechanical force applied to the area of skin by the skin permeabilizing device based on the at least one electrical parameter,
   wherein after the permeability of the skin is increased, the analyte or drug is able to passively diffuse through the skin.

2. The method of claim 1, further comprising:
   applying electricity to the area of skin before increasing the permeability of the area of skin with a skin permeabilizing device; and
   measuring a baseline for the at least one electrical parameter.

3. The method of claim 1, further comprising:
   coupling a first electrode with the area of skin;
   coupling a second electrode with the area of skin; and
   measuring the at least one electrical parameter using the first electrode and the second electrode.

4. The method of claim 3, wherein the first electrode is coupled with a portion of stratum corneum of the area of skin.

5. The method of claim 4, wherein the second electrode is coupled with a portion of epidermis over which the stratum corneum has been removed.

6. The method of claim 4, wherein the second electrode is coupled with a portion of stratum corneum of the skin.

7. The method of claim 3, wherein at least one of the first and second electrode is coupled through a conductive medium.

8. The method of claim 7, wherein the conductive medium is a gel.

9. The method of claim 7, wherein the conductive medium is a liquid.

10. The method of claim 3, wherein the second electrode is placed on the skin.

11. The method of claim 1, further comprising:
    comparing the at least one electrical parameter with a baseline, and
    wherein the step of controlling the skin permeabilizing device comprises discontinuing the application of the skin permeabilizing device based on the comparison.

12. The method of claim 1, wherein the electrical parameter is selected from the group consisting of impedance, conductance, capacitance, current, and voltage.

13. The method of claim 1, wherein said application of said skin permeabilizing device is continuous.

14. The method of claim 1, wherein said application of said skin permeabilizing device is discontinuous.

15. The method of claim 14, further comprising the steps of
    performing analog to digital conversion on said information on a time-variation of skin conductance; and
    filtering said digital data.

16. The method of claim 1, further comprising a step of processing data from the monitoring step to establish information on a time-variation of skin conductance.

17. The method of claim 16, wherein the step of processing comprises fitting said information into the following equation:

$$C = C_i + \frac{(C_f - C_i)}{1 + e^{S(t-t^*)}}$$

where:
C is current;
$C_i$ is current at t=0;
$C_f$ is the final current;
S is a sensitivity constant;
t* is the exposure time required to achieve an inflection point; and
t is the time of exposure.

18. An apparatus for enhancing permeability of an area of skin comprising:
    a skin permeabilizing device configured to increase a permeability of the area of skin using mechanical force;
    an electrical source operable to apply electricity in the form of an alternating current to the area of skin;
    a permeability monitoring circuit to monitor at least one electrical parameter of the area of skin indicative of skin permeability; and
    a controller responsive to the permeability monitoring circuit and operable to control the mechanical force applied to the area of the skin by the skin permeabilizing device based on the at least one electrical parameter of the area of skin.

19. The apparatus of claim 18, wherein the electrical source comprises:
   a first source having a first frequency; and
   a second source having a second frequency.

20. The apparatus of claim 19, wherein the circuit measures the at least one electrical parameter of the area of skin at the first frequency and at the second frequency.

21. The apparatus of claim 18, further comprising:
   a first electrode, wherein in use the first electrode is coupled on the area of skin; and
   a second electrode, wherein in use the second electrode is positioned on the skin;
   wherein in use the circuit measures the at least one electrical parameter of the area of skin between the first electrode and the second electrode.

22. The apparatus of claim 18, wherein the parameter is selected from the group consisting of impedance, conductance, capacitance, current, and voltage.

* * * * *

UNITED STATES PATENT AND TRADEMARK OFFICE
CERTIFICATE OF CORRECTION

| | | Page 1 of 1 |
|---|---|---|
| PATENT NO. | : 8,287,483 B2 | |
| APPLICATION NO. | : 10/792862 | |
| DATED | : October 16, 2012 | |
| INVENTOR(S) | : Mitragotri et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1951 days.

Signed and Sealed this
Second Day of September, 2014

Michelle K. Lee
*Deputy Director of the United States Patent and Trademark Office*